United States Patent
Xiao et al.

(10) Patent No.: US 7,910,801 B2
(45) Date of Patent: Mar. 22, 2011

(54) PLANTS WITH REDUCED EXPRESSION OF PHOSPHATASE TYPE 2C GENE FOR ENHANCED PATHOGEN RESISTANCE

(75) Inventors: Shunyuan Xiao, Rockville, MD (US); Wenming Wang, Rockville, MD (US)

(73) Assignee: University of Maryland, College Park, College Park, MD (US)

(*) Notice: Subject to any disclaimer, the term of this patent is extended or adjusted under 35 U.S.C. 154(b) by 362 days.

(21) Appl. No.: 11/762,989

(22) Filed: Jun. 14, 2007

(65) Prior Publication Data

US 2007/0256193 A1 Nov. 1, 2007

Related U.S. Application Data

(63) Continuation-in-part of application No. PCT/US2005/045001, filed on Dec. 13, 2005.

(60) Provisional application No. 60/635,768, filed on Dec. 14, 2004.

(51) Int. Cl.
*A01H 1/00* (2006.01)
*C12N 15/82* (2006.01)
*C12N 15/87* (2006.01)

(52) U.S. Cl. .................. 800/279; 800/285; 800/278

(58) Field of Classification Search .................. None
See application file for complete search history.

(56) References Cited

U.S. PATENT DOCUMENTS

| | | | |
|---|---|---|---|
| 4,407,956 A | 10/1983 | Howell | |
| 2004/0209325 A1 | 10/2004 | Yang et al. | |

OTHER PUBLICATIONS

Hu et al. 2006, Pyhysiologia Plantarum 127:225-236.*
Thomas et al. 2001,The Plant Journal 25(4):417-425.*
Alber, T.; Kawasaki, G. 1982. Nucleotide sequence of the triose phosphate isomerase gene of *Saccharomyces cerevisiae*. *J. Mol. Appl. Genet.*, 1(5): 419-34.
Bertauche N., Leung J., Giraudat J. 1996. Protein phosphatase activity of abscisic acid insensitive 1 (ABI1) protein from *Arabidopsis thaliana*. *Eur. J. Biochem.*, 241(1): 193-200.
Chern, M.-S.; Fitzgerald, H. A.; Yadav, R. C.; Canlas, P. E.; Dong, X.; Ronald, P. C. 2001. Evidence for a disease-resistance pathway in rice similar to the NPR1-mediated signaling pathway in *Arabidopsis. Plant J.*, 27(2): 101-13.
Clough, S. J.; Bent A. F. 1998. Floral dip: a simplified method for Agrobacterium-mediated transformation of *Arabidopsis thaliana. Plant J.*, 16(6): 735-43.
Crossway, A.; Oakes, J.; Irvine, J.; Ward, B.; Knauf, V.; Shewmaker, C.K. 1986. Integration of foreign DNA following microinjection of tobacco meophyll photoplasts. *Mol. Gen. Genet.*, 202:179-85.
Dangl J. L.; Jones J. D. G. 2001. Plant pathogens and integrated defence responses to infection. *Nature*, 411(6839): 826-833.
Dangl J. L., Dietrich R. A., and Richberg M. H. 1996. Death don't have no mercy: Cell death programs in plant-microbe interactions. *Plant Cell*, 8(10): 1793-1807.

Ferrando, A.; Farràs, R.; Jásik, J.; Schell, J.; Koncz, C. 2000. Intron-tagged epitope: a tool for facile detection and purification of proteins expressed in Agrobacterium-transformed plant cells. *Plant J.*, 22(6): 553-60.
Fraley R. T., Dellaporta S. L., and Papahadjopoulos D. 1982. Liposome-Mediated Delivery of Tobacco Mosaic Virus RNA into Tobacco Protoplasts: A Sensitive Assay for Monitoring Liposome-Protoplast Interactions. *Proc. Natl. Acad. Sci. USA*, 79(6):1859-1863.
Fraley R. T., Rogers S. G., Horsch R. B., Sanders P. R., Flick J. S., Adams S. P., Bittner M. L., Brand L. A., Fink C. L., Fry J. S., Galluppi G. R., Goldberg S. B., Hoffmann N. L., and Woo S. C. 1983. Expression of bacterial genes in plant cells. *Proc. Nat. Acad. Sci. USA*, 80(15):4803-4807.
Fromm M., Taylor L. P., and Walbot V. 1985. Expression of genes transferred into monocot and dicot plant cells by electroporation. *Proc. Natl Acad. Sci. USA*, 82(17):5824-5828.
Glazebrook J. 2001. Genes controlling expression of defense responses in *Arabidopsis*—2001 status. *Curr. Opin. Plant Bio.*, 4(4): 301-308.
Grant, M.; Adams, I.; Knight, M.; Ainslie, A.; Mansfield, J. 2000. The RPM1 plant disease resistance gene facilitates a rapid and sustained increase in cytosolic calcium that is necessary for the oxidative burst and hypersensitive cell death. *Plant J.*, 23(4): 441-450.
Greenberg J. T., Guo A. L., Klessig D. F. 1994. Programmed cell-death in plants—a pathogen-triggered response activated coordinately with multiple defense functions. *Cell*, 77(4): 551-563.
Gielen J., Debeuckeleer M., Seurinck J. 1984. The complete nucleotide sequence of the TL-DNA of the *Agrobacterium tumefaciens* plasmid pTiAch5. *EMBO J.*, 3:835-846.
Hammond-Kosack K.E., and Jones J. D. G. 1997. Plant disease resistance genes. *Annual Review of Plant Physiology and Plant Molecular Biology*, 48(1): 575-607.
Herrera-Estrella L., Depicker A., Van Montagu M. and Schell J. 1983. Expression of chimaeric genes transferred into plant cells using a Ti-plasmid-derived vector. *Nature*, 303(5914):209-213.
Hoekema A., Hirsch P. R., Hooykaas P. J. J. and Schilperoort R. A. 1983. A binary plant vector strategy based on separation of *vir*- and T-region of the *Agrobacterium tumefaciens* Ti-plasmid. *Nature*, 303(5913): 179-181.
Jirage D., Tootle T. L., Reuber T. L., Frost L. N., Feys B. J., Parker J. E., Ausubel F. M., and Glazebrook J. 1999. *Arabidopsis thaliana* PAD4 encodes a lipase-like gene that is important for salicylic acid signaling. *Proc. Natl. Acad. Sci. U.S.A*, 96(23) : 13583-13588.

(Continued)

*Primary Examiner* — Li Zheng

(74) *Attorney, Agent, or Firm* — Marianne Fuierer; Moore & Van Allen, PLLC

(57) ABSTRACT

The present invention relates to a method for down regulating an *Arabidopsis* protein phosphatase type 2C gene, referred to as "defense-associated protein phosphatase type 2C one" (DAPP1) that functions as a negative regulator of a plant defense pathway by contacting the gene or gene mRNA with an interfering nucleotide sequence that interacts with the gene and reducing expression thereof. Plants including such interfering nucleotide sequence exhibit increased disease resistance to pathogen even in the absence of R genes. Close homologs of DAPP1 exist in multiple crop species, and as such, the controlled down-regulation of homologous genes in a variety of crop species will enhance disease resistance of target crop species to pathogens.

6 Claims, 13 Drawing Sheets

OTHER PUBLICATIONS

Kerk D., Bulgrien J., Smith D. W., Brooke Barsam, Stella Veretnik, and Michael Gribskov. 2002. The complement of protein phosphatase catalytic subunits encoded in the genome of *Arabidopsis*. *Plant Physiol.*, 129(2): 908-925.

Klein T. M., Wolf E. D., Wu R. and Sanford J. C.. 1987. High-velocity microprojectiles for delivering nucleic acids into living cells. *Nature*, 327(6117):70-73.

Krens F. A., Molendijk L., Wullems G. J. and Schilperoort R. A. 1982. In vitro transformation of plant products with Ti-plasmid DNA. *Nature*, 296(5852):72-74.

Lamb, C.; Dixon, R. A. 1997. The oxidative burst in plant disease resistance. *Annu. Rev. Plant Physiol Plant Mol. Biol.*, 48(1): 251-275.

Lam E., Kato N. and Lawton M. 2001. Programmed cell death, mitochondria and the plant hypersensitive response. *Nature*, 411(6839): 848-853.

McDowell J. M. and Dangl J. L. 2000. Signal transduction in the plant immune response. *Trends Biochem Sci.*, 25(2): 79-82.

Mylne J. and Botella J. R. 1998. Binary vectors for sense and antisense expression of *Arabidopsis* ESTs. *Plant Mol. Biol. Rep.*, 16(3): 257-262.

Morel J. B. and Dangl J. L. 1997. The hypersensitive response and the induction of cell death in plants. *Cell Death Differ.*, 4(8): 671-683.

Nawrath C., Hack S., Parinthawong N., Jean-Pierre Métraux. 2002. EDS5, an essential component of salicylic acid-dependent signaling for disease resistance in *Arabidopsis*, is a member of the MATE transporter family. *Plant Cell*, 14(1): 275-286.

Needleman S. B. and Wunsch C. D. 1970. A general method applicable to search for similarities in amino acid sequence of 2 proteins. *J. Mol. Biol.*, 48(3):443-453.

Odell J. T., Nagy F. and Chua N.-H.. 1985. Identification of DNA sequences required for activity of the cauliflower mosaic virus 35S promoter. *Nature*. 313(6005):810-812.

Pearson W. R. and Lipman D. J. 1988. Improved tools for biological sequence comparison. *Proc. Natl. Acad. Sci. U.S.A.*, 85(8):2444.

Peart J. R., Lu R., Sadanandom A., Malcuit I., Moffett P., Brice D. C., Schauser L., Jaggard D. A. W., Xiao S., Coleman M. J., Dow M., Jones J. D. G., Shirasu K., and Baulcombe D. C. 2002. Ubiquitin ligase-associated protein SGT1 is required for host and nonhost disease resistance in plants. *Proc. Natl. Acad. Sci. U.S.A*, 99(16): 10865-10869.

Ruvkun G. B. and Ausubel F. M. 1981. A general method for site-directed mutagenesis in prokaryotes. *Nature*, 289(5793):85-88.

St. Schell J. 1987. Transgenic plants as tools to study the molecular organization of plant genes. *Science*, 237(4819) :1176-1183.

Tai T. H., Dahlbeck D., Clark E. T., Gajiwala P., Pasion R., Whalen M. C., Stall R. E., and Staskawicz B. J. 1999. Expression of the *Bs2* pepper gene confers resistance to bacterial spot disease in tomato. *Proc. Natl. Acad. Sci. U.S.A*, 96(24): 14153-14158.

Van der Biezen, Erik A; Freddie, Cecilie T; Kahn, Katherine; Parker, Jane E; Jones, Jonathan D. G. 2000. *Arabidopsis* RPP4 is a member of the RPP5 multigene family of TIr-Nb-LRR genes and confers downy mildew resistance through multiple signalling components. *Plant J.*, 29(4): 439-51.

Xiao S., Ellwood S., Calis O., Patrick E., Li T., Coleman M., Turner J. G. 2001. Broad spectrum mildew resistance in *Arabidopsis thaliana* mediated by RPW8. *Science*, 291(5501):118-120.

Zhang S. Q. and Klessig D. F. 2001. MAPK cascades in plant defense signaling. *Trends in Plant Sci.*, 6(11): 520-527.

Tahtiharju S. and Palva T. 2001. Antisense inhibition of protein phosphatase 2C accelerates cold acclimation in *Arabidopsis thaliana. Plant J.*, 26(4): 461-470.

Yamada et al. 2002. *Arabidopsis thaliana* clone U19121 putative protein phosphatase type 2C (At1g22280) mRNA, complete cds. GenBank Accession AY133737.

Yamada et al. 2002. Putative protein phosphate type 2C (*Arabidopsis thaliana* ). Accession AAM91671.

*Arabidopsis thaliana* protein phosphatase 2C, putative/PP2C, putative (AT1G22280) mRNA, complete cds., NM_202154, 2008.

DePicker et al., 1982, Mol. and Appl. Genet., 1:561-573.

Hohn et al., 1982 "Molecular Biology of Plant Tumors," Academic Press, New York, pp. 549-560.

MacKintosh, 1993, Protein Phosphorylation: A Practical Approach, D. G. Hardie, ed. Oxford, Oxford University Press, pp. 197-230.

Smith T.F.; Waterman, M.S. 1981. Combinations of biosequences. Adv. Appl. Math., 2(4): 482-89.

* cited by examiner

Short day

Long day

SEQUENCE LISTING

<160> NUMBER OF SEQ ID NOS: 4

<210> SEQ ID NO 1
<211> LENGTH: 660
<212> TYPE: DNA
<213> ORGANISM: Arabidopsis thaliana

<400> SEQUENCE: 1

```
atgggaaaat tttgttgctt cacttccgct tctgaggttg tgggaggaca atcatcatca      60
cgatcaggta aaggaagaag tgatgaaggg atgatcaagt atggttttag tctagtgaaa     120
ggaaaagcta accatccaat ggaagattat catgttgcta actttatcaa catccaagac     180
catgaattgg gtcttttttgc tatttatgat ggtcatatgg gtgatagtgt ccctgcttac     240
ttgcagaaac gtctcttctc caatatcctt aaggagggag agttttgggt tgatcctcga     300
aggtctattg caaaagctta tgagaagacg gaccaagcga ttctatcgaa tagttctgac     360
ttgggtcgtg gtggttctac tgctgtgact gctatattga ttaatgggag aaagttgtgg     420
atagctaatg ttggtgattc acgagctgtt ctttctcatg gtggcgctat aacgcagatg     480
agtacagatc atgagcctcg tactgaaagg tcgagtattg aagatagagg tggatttgta     540
tccaatctac caggtgatgt tcctcgggtg aatggtcaat tagctgtgtc tcgtgctttt     600
ggagataagg gacttaagac acacttgagt tcagagcctg acataaaaga agctactgta     660
```

<210> SEQ ID NO 2
<211> LENGTH: 281
<212> TYPE: PRT
<213> ORGANISM: Arabidopsis thaliana

<400> SEQUENCE: 2

```
Met Gly Lys Phe Cys Cys Phe Thr Ser Ala Ser Glu Val Val Gly Gly
1               5                   10                  15

Gln Ser Ser Ser Arg Ser Gly Lys Gly Arg Ser Asp Glu Gly Met Ile
            20                  25                  30

Lys Tyr Gly Phe Ser Leu Val Lys Gly Lys Ala Asn His Pro Met Glu
        35                  40                  45

Asp Tyr His Val Ala Asn Phe Ile Asn Ile Gln Asp His Glu Leu Gly
    50                  55                  60

Leu Phe Ala Ile Tyr Asp Gly His Met Gly Asp Ser Val Pro Ala Tyr
65                  70                  75                  80

Leu Gln Lys Arg Leu Phe Ser Asn Ile Leu Lys Glu Gly Glu Phe Trp
                85                  90                  95

Val Asp Pro Arg Arg Ser Ile Ala Lys Ala Tyr Glu Lys Thr Asp Gln
            100                 105                 110

Ala Ile Leu Ser Asn Ser Ser Asp Leu Gly Arg Gly Gly Ser Thr Ala
        115                 120                 125

Val Thr Ala Ile Leu Ile Asn Gly Arg Lys Leu Trp Ile Ala Asn Val
    130                 135                 140
```

-continued

```
Gly Asp Ser Arg Ala Val Leu Ser His Gly Gly Ala Ile Thr Gln Met
145                 150                 155                 160

Ser Thr Asp His Glu Pro Arg Thr Glu Arg Ser Ser Ile Glu Asp Arg
                165                 170                 175

Gly Gly Phe Val Ser Asn Leu Pro Gly Asp Val Pro Arg Val Asn Gly
            180                 185                 190

Gln Leu Ala Val Ser Arg Ala Phe Gly Asp Lys Gly Leu Lys Thr His
        195                 200                 205

Leu Ser Ser Glu Pro Asp Ile Lys Glu Ala Thr Val Asp Ser Gln Thr
    210                 215                 220

Asp Val Leu Leu Leu Ala Ser Asp Gly Ile Trp Lys Val Met Thr Asn
225                 230                 235                 240

Glu Glu Ala Met Glu Ile Ala Arg Arg Val Lys Asp Pro Gln Lys Ala
                245                 250                 255

Ala Lys Glu Leu Thr Ala Glu Ala Leu Arg Arg Glu Ser Lys Asp Asp
            260                 265                 270

Ile Ser Cys Val Val Val Arg Phe Arg
            275                 280

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
cgaattcatg ggaaaatttt gttgcttcac t                              31

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4
cgggatcctc atctgaatcg gaccacgaca                                30
```

PLANTS WITH REDUCED EXPRESSION OF PHOSPHATASE TYPE 2C GENE FOR ENHANCED PATHOGEN RESISTANCE

CROSS REFERENCE TO RELATED APPLICATIONS

The present application claims priority to PCT Application No. PCT/US05/045001 filed in the U.S. Patent and Trademark Office, PCT Division, on Dec. 13, 2005, which in turn claims priority to U.S. Provisional Patent Application No. 60/635,768 filed on Dec. 14, 2004, the contents of which are hereby incorporated by reference herein.

BACKGROUND OF THE INVENTION

1. Field of Invention

The present invention relates generally to modifying plants, and more particularly, to modifying expression of genes to enhance disease resistance therein.

2. Related Art

Plants have evolved a sophisticated innate immune system to defend themselves from the attack of potential pathogens. On top of this system are disease resistance (R) genes that recognize specific pathogen strains and initiate a battery of defense responses including a rapid production of reactive oxygen species (oxidative burst), induction of pathogenesis-related (PR) genes and a more readily detectable hypersensitive response (HR) (Hammond-Kosack and Jones, 1997; McDowell and Dangl, 2000; Glazebrook, 2001). HR is often manifested as rapid, localized death of plant cells at the infection site that contains the invading pathogen, and is believed to be a form of programmed cell death (PCD) analogous to animal apoptosis (Morel and Dangl, 1997; Lam et al., 2001).

A current challenge is to understand the mechanisms that link R gene-mediated pathogen recognition to the expression of resistance and the accompanying HR. At least 5 structurally distinct classes of R proteins have been characterized. The majority of isolated R genes encode members of a superfamily of nucleotide binding site and leucine-rich repeat (NB-LRR) containing proteins (Dangl and Jones, 2001). Interestingly, plant defense responses triggered by different types of R genes upon recognition of pathogens carrying corresponding avirulence (Avr) genes are often very similar (Hammond-Kosack and Jones, 1997; McDowell and Dangl, 2000; Glazebrook, 2001). This suggests that different types of R genes may activate common downstream signaling pathways that lead to the expression of resistance.

In 2001, a novel type of plant R gene RPW8 that confers broad-spectrum resistance in *Arabidopsis* to powdery mildew (*Erysiphe*) pathogens (Xiao et al., 2001) was discovered by one of the present inventors. The predicted products of the gene RPW8 of *Arabidopsis* are small, basic proteins with a putative N-terminal transmembrane domain and a coiled coil domain (Xiao et al., 2001). They lack the nucleotide binding site and Leu-rich repeats that characterize the products of the other *Arabidopsis* R genes (Dangl and Jones, 2001). RPW8 confers resistance to all tested isolates of the four species of powdery mildew pathogens of *Arabidopsis* (Xiao et al., 2001). By contrast, most other R genes confer resistance to only one or a few isolates of a pathogen species carrying the corresponding Avr genes (Hammond-Kosack and Jones, 1997). Despite these differences, resistance mediated by RPW8 is characterized by an HR involving the formation of $H_2O_2$. The HR triggered by the RPW8 genes involves the defense signaling components salicylic acid (SA) and EDS1 (Xiao et al., 2001). Thus, disease resistance regulated by the RPW8 genes is similar to that regulated by the other *Arabidopsis* R genes. Although the mechanisms by which R proteins induce HR are largely unknown, influx of calcium, protein phosphorylation and dephosphorylation, production of reactive oxygen intermediates and nitric oxide, and SA synthesis are associated with the onset of HR (Greenberg et al., 1994; Dangl et al., 1996; Lamb and Dixon, 1997; Grant et al., 2000; Glazebrook, 2001; Zhang and Klessig, 2001).

Discovery and understanding the effects of different types of R genes is important, however, modulating the activity of such genes is only possible when the interactions with other components in the plant cells are determined. Further, plant defense systems cannot be adequately activated upon pathogen attack in plants lacking cognate disease resistance (R) genes. Unfortunately, the majority of commercial crop cultivars possess fewer R genes and they are thus generally more susceptible to pathogens as compared with their wild relatives.

Utilization of R genes to protect plants against pathogens has certain limitations as well. First, plant R genes often do not function in unrelated plant genera due to "restricted taxonomic functionality" (Tai et al., 1999). Second, introduction of R genes from resistant germplasm into commercial cultivars requires time-consuming breeding programs. Third, most R genes confer resistance to only one or a few strains of a particular pathogen (Dangl and Jones, 2001). Fourth, R gene-mediated resistance is often overcome by pathogens in a short period of time.

Recent studies in this field have revealed that the signal transduction pathway(s) of plant R genes is highly conserved among different plant species (Chern et al., 2001; Liu et al., 2002). Therefore, there is a potential and a need in the art for determining interacting components that modify the activities of R genes and provide a means for enhancing pathogen resistance by controlling (e.g. up- or down-regulating) the determined key downstream components of the R gene signaling pathway(s).

SUMMARY OF THE INVENTION

Plant R gene-mediated pathogen resistance is tightly regulated by both positive and negative components in the R-gene signaling pathway. Genetic manipulation of key regulators of this pathway can provide a novel strategy to enhance disease resistance even in the absence of R genes.

Thus, the present invention relates to the discovery of that an *Arabidopsis* protein phosphatase type 2C gene, hereinafter referred to as "defense-associated protein phosphatase type 2C one" (DAPP1). DAPP1, functions as a negative regulator of a plant defense pathway. Further, the down-regulation of this DAPP1 gene results in enhanced disease resistance to a broad range of pathogens. Importantly, close homologs of DAPP1 exist in multiple crop species, and as such, the controlled down-regulation of homologous genes in a variety of crop species will enhance disease resistance of target crop species to pathogens.

In one aspect, the present invention relates to a method of enhancing disease resistance to pathogen in a plant, the method comprising altering the genetic expression of DAPP1 or a DAPP1 homolog. Preferably, altering the genetic expression is effected by inhibiting expression of the DAPP1 gene by introducing an interfering nucleotide sequence that targets at least a fragment of the polynucleotide sequence of the DAPP1 gene or DAPP1 homolog and silences the gene. The interfering polynucleotide sequence may include, but is not limited to, antisense DNA or RNA, interfering double-stranded (siRNA) and single-stranded micro RNA (miRNA), ribozymes, chimeric sequences, or derivatives of these groups.

A preferred DAPP1 homolog exhibits the functionality of negatively regulating R genes including RPW8 genes.

In the alternative, the nucleotide sequence of the DAPP1 gene or homolog thereof may be altered by introducing a mutation in the DAPP1 gene in a manner that prevents expression of the DAPP1 gene or alters interaction with an R gene in a plant cell.

In another aspect the present invention relates to a method for increasing disease resistance in a plant comprising:

introducing into the plant an expression cassette comprising a promoter sequence operably linked to an interfering nucleotide sequence that interacts with at least a fragment of a nucleotide sequence encoding a DAPP1 gene or DAPP1 homolog thereof, wherein the interfering nucleotide sequence inhibits expression of the DAPP1 gene or DAPP1 homolog thereof relative to a control plant not including the interfering nucleotide sequence.

In yet another aspect the present invention relates to a plant comprising an expression cassette comprising an interfering polynucleotide sequence that interferes with at least a fragment of a polynucleotide sequence encoding a DAPP1 gene or a DAPP1 gene homolog, wherein plants having a reduced mRNA levels of the DAPP1 gene or DAPP1 gene homolog exhibit increased expression of defense-related genes. Preferably, the interfering polynucleotide sequence that interacts with the DAPP1 gene or DAPP1 gene homolog is operably linked to a promoter sequence. More preferably, the polynucleotide sequence of DAPP1 gene is SEQ ID NO. 1 or a polynucleotide sequence having at least 75% identity thereto, and more preferably, at least 90% identity, wherein down regulation of the DAPP1 gene enhances disease resistance to pathogens.

In still another aspect, the present invention relates to a recombinant expression cassette comprising a plant promoter sequence operably linked to an interfering polynucleotide sequence that interacts with the polynucleotide sequence of the DAPP1 gene or a DAPP1 gene homolog, wherein the DAPP1 gene or a DAPP1 gene homolog functions as a negative regulator of a plant defense pathway and down-regulation of the DAPP1 gene or a DAPP1 gene homolog results in enhanced disease resistance to pathogens.

Another aspect of the present invention relates to a plant cell comprising the expression cassette described herein. The expression cassette can be introduced into the plant using in vitro techniques (e.g. using *Agrobacterium*) or by a sexual cross. The promoter may be constitutive (e.g., the 35S promoter of cauliflower mosaic virus) or inducible.

In a still further aspect, the present invention relates to a method of enhancing disease resistance to pathogens, the method comprising the steps of:

introducing a vector comprising a complementary polynucleotide sequence in an antisense orientation to the nucleotide sequence of a DAPP1 gene or a homolog thereof, wherein the complementary polynucleotide sequence is controlled by a promoter; and decreasing the level of protein production encoded by the nucleotide sequence of the DAPP1 gene or a homolog thereof by reducing expression of the DAPP1 gene or a homolog thereof.

In another aspect, the present invention further provides an expression vector containing at least a fragment of an interfering polynucleotide sequence that causes the inhibition of the expression of SEQ ID NO. 1 or a sequence having at least 95% homology to SEQ ID NO. 1.

In another aspect this expression vector is contained within a host cell and transforms the host cell to inhibit expression of a polypeptide having an amino acid sequence selected from the group consisting of SEQ ID NO: 2 or an amino acid sequence having at least 90% homology thereof.

A still further aspect relates to a method for identifying nucleotide sequences that silences expression of a DAPP1 gene or DAPP1 homolog thereof, the method comprises: (a) exposing the DAPP1 gene or DAPP1 homolog to a plurality of testing nucleotide sequences; (b) measuring levels of mRNA; and (c) selecting testing nucleotide sequences that demonstrate the ability to reduce mRNA levels of DAPP1 or DAPP1 homologs.

This invention further provides kits containing any of the vectors or expression cassettes described herein. Such kits can further comprise instructions and control materials.

Other features and advantages of the invention will be apparent from the following detailed description, drawings and claims.

DETAILED DESCRIPTION OF THE INVENTION

Definitions

Figure 1:
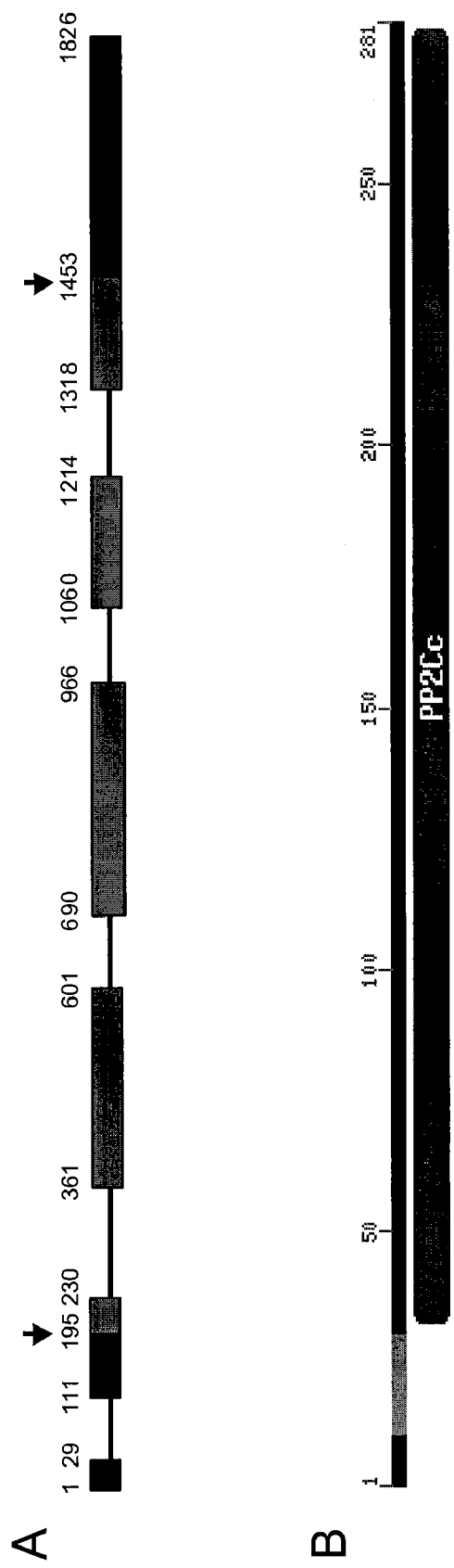
FIG. 1 shows the schematic structure of the At1g22280 gene (A) and its predicted protein (B).

While the following terms are believed to have well defined meanings in the art, the following definitions are set forth to facilitate explanation of the invention.

Following long-standing patent law convention, the terms "a" and "an" mean "one or more" when used in this application, including the claims.

The term "promoter," as used herein refers to a region of DNA upstream from the structural gene and involved in recognition and binding RNA polymerase and other proteins to initiate transcription. A "plant promoter" is a promoter capable of initiating transcription in plant cells. An "inducible" promoter is a promoter which is under more precise environmental or developmental control. Examples of environmental conditions that may effect transcription by inducible promoters include anaerobic conditions or the presence of light. Examples of promoters under developmental control include promoters that initiate transcription only in certain tissues, such as root specific promoters.

The term "plant," as used herein, includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "expression," as used herein, refers to the transcription and translation of a structural gene so that a protein is synthesized.

The term "antisense orientation," as used herein, refers to the orientation of nucleic acid sequence from a gene that is inserted in an expression cassette in an inverted manner with respect to its naturally occurring orientation.

The term "operably linked," as used herein, refers to functional linkage between a promoter and a second sequence, wherein the promoter sequence initiates transcription of RNA corresponding to the second sequence.

The term "modulate," as used herein, means an increase, decrease, or other alteration of any or all chemical and biological activities or properties of a wild-type or mutant gene or protein. The term "modulation" as used herein refers to both upregulation (i.e., activation or stimulation) and down-regulation (i.e. inhibition or suppression) of a response.

The terms "cells," "host cells" or "recombinant host cells," as used herein, are used interchangeably and mean not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

The term "interact," as used herein, means detectable interactions between molecules, such as can be detected using, for example, a yeast two-hybrid assay. The term "interact" is also meant to include "binding" interactions between molecules. Interactions can, for example, be protein-protein, protein-nucleic acid or nucleic acid-nucleic acid in nature.

The term "modified," as used herein, means an alteration in a nucleotide or amino acid sequence which includes adding or removing discrete amino acid residues or nucleotide units. The term "modified" encompasses detectable labels as well as those entities added as aids in purification.

The term "mutation," as used herein, carries its traditional connotation and means a change, inherited, naturally occurring or introduced, in a nucleic acid or polypeptide sequence, and is used in its sense as generally known to those of skill in the art.

The term "polypeptide," as used herein, refers to peptides, polypeptides and proteins, unless otherwise noted. As used herein, the terms "protein," "polypeptide" and "peptide" are used interchangeably herein when referring to a gene product.

The term "polynucleotide," as used herein, means a sequence of nucleotides connected by phosphodiester linkages. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

The term "complementary sequence," as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

The term "gene," as used herein, refers broadly to any segment of DNA associated with a biological function. A gene encompasses sequences including but not limited to a coding sequence, a promoter region, a cis-regulatory sequence, a non-expressed DNA segment is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "gene expression," as used herein, refers to the process of converting genetic information encoded in a gene into RNA (e.g., mRNA, rRNA, tRNA, or snRNA) through "transcription" of a deoxyribonucleic gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (ie., RNA or protein), while "down-regulation" or "repression" refers to regulation that decrease production. Molecules (e.g., transcription factors) that are involved in up-regulation or down-regulation are often called "activators" and "repressors," respectively.

The term "substantial identity," as used herein means that a polynucleotide or polypeptide comprises a sequence that has at least 80% sequence identity, preferably at least 90% or more preferably at least 97%, compared to a reference sequence over a comparison window.

The term "inhibit" or "inhibiting," as used herein, means that a response is decreased or prevented due to the presence of an interfering nucleotide sequence as opposed to in the absence of the interfering nucleotide sequence.

General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., 1989.

The present invention relates to a method for reducing expression of the DAPP1 gene or DAPP1 homologues thereof by with an interfering nucleotide sequence that inhibits the translation in the plant cell of a polyribonucleotide encoding a DAPP1 polypeptide. One embodiment relates to an interfering nucleotide sequence comprising at least one antisense strand that functions to pair with the target DAPP1 mRNA, and thereby down-regulate or block the expression of the DAPP1 polypeptide. The interfering nucleotide sequence includes an antisense polynucleotide, a ribozyme, and a small interfering RNA (siRNA), wherein said interfering nucleotide sequence comprises a nucleic acid sequence complementary to, or engineered from SEQ ID NO. 1 or a nucleotide sequence having at least 75% identity thereto.

The present invention relates to a method wherein the interfering nucleotide sequence is selected from the group consisting of antisense RNA, antisense oligodeoxynucleotide (ODN), a ribozyme that cleaves the polyribonucleotide coding for SEQ ID NO: 1, a small interfering RNA (siRNA) that is sufficiently homologous to a portion of the polyribonucleotide corresponding to SEQ ID NO: 1 such that the siRNA interferes with the translation of the DAPP1 polyribonucleotide to the DAPP1 polypeptide.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding a DAPP1 polypeptide or the corresponding messenger RNA. In addition, antisense nucleic acids may be designed which decrease expression of the nucleic acid sequence capable of encoding a DAPP1 polypeptide by inhibiting splicing of its primary transcript. Any length of antisense sequence is suitable for practice of the invention so long as it is capable of down-regulating or blocking expression of SEQ ID NO. 1 or a sequence having at least 90% identity thereof. The preparation and use of antisense nucleic acids, DNA encoding antisense RNAs and the use of oligo and genetic antisense is known in the art.

One embodiment of an interfering nucleotide sequence is a nucleic acid that is antisense to a nucleic acid comprising SEQ ID NO: 1. For example, an antisense nucleic acid (e.g. DNA) may be introduced into cells in vitro or in vivo. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 10 to about 30 contiguous nucleotides selected from the sequence of SEQ ID NO: 1, expressed in the opposite orientation.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (RNase) H, which cleaves the mRNA component of the hybrid molecule.

Another type of interfering nucleotide sequence is a ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base-pairing. Once it is bound to the correct target site, the ribozyme acts enzymatically to cut the target mRNA. Cleavage of the mRNA by a ribozyme destroys its ability to direct synthesis of the corresponding polypeptide. Once the ribozyme has cleaved its target sequence, it is released and can repeatedly bind and cleave at other mRNAs.

Ribozymes may be chemically synthesized by combining an oligodeoxyribonucleotide with a ribozyme catalytic domain (20 nucleotides) flanked by sequences that hybridize to the target mRNA after transcription. The oligodeoxyribonucleotide is amplified by using the substrate binding sequences as primers. The amplification product is cloned into an expression vector.

Ribozymes are expressed from transcription units inserted into DNA, RNA, or viral vectors. Transcription of the ribozyme sequences are driven from RNA polymerase promoters.

A particularly preferred interfering nucleotide sequence is a small interfering RNA (siRNA). siRNAs mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from SEQ ID NO. 1 and an antisense strand of 17-23 nucleotides complementary to the sense strand. The most preferred siRNA comprises sense and anti-sense strands that are 100 percent complementary to each other and the DAPP1 polynucleotide sequence. Preferably the siRNA further comprises a loop region linking the sense and the antisense strand.

A self-complementing single stranded siRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 nucleotides long. Self-complementary single stranded siRNAs form hairpin loops and are more stable than ordinary dsRNA. In addition, they are more easily produced from vectors.

The present invention also relates to compositions, and methods using said compositions, comprising a DNA expression vector capable of expressing an interfering nucleotide sequence capable of inhibiting DAPP1 protein precursor processing.

The nucleic acid sequence expressing the interfering nucleotide sequence is preferably included within a vector. Selection of an appropriate vector useful in the present invention is relatively simple, as the constraints are minimal. The minimal requirements of the vector are that the desired nucleic acid sequence be introduced in a relatively intact state. Thus, any vector which will produce a plant carrying the introduced nucleotide sequence should be sufficient. Any vector which will introduce a substantially intact RNA which can ultimately be converted into a stably maintained nucleotide sequence is also acceptable. The decision as to whether to use a vector, or which vector to use, will be guided by the method of transformation selected. This determination is considered to be well with in the ordinary skill of those in the art.

The vectors useful in the present invention include, but are not limited to, the Ti plasmid vectors and shuttle vectors designed for particle gun transformation. The selection of vectors and methods to construct them are commonly known to persons of ordinary skill in the art and are described in general technical references (See, Wu and Grossman, 1987).

The vectors typically comprise additional attached sequences which confer resistance to degradation of the nucleic acid fragment, which assist in the process of genomic integration, or which provide a means to easily select for those cells or plants which are transformed. Such sequences are advantageous and greatly decrease the difficulty of selecting useable transformed plants.

The recombinant vectors of the present invention typically comprise an expression cassette designed for initiating transcription of the desired polynucleotide sequences in plants. Other nucleotide sequences encoding additional functions may also be present in the vector, as is known in the art. For instance, in the case of Agrobacterium transformations, T-DNA sequences will also be included for subsequent transfer to plant chromosomes. For expression in plants, the recombinant expression cassette will contain, in addition to the desired polynucleotide sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

The particular promoter used in the expression cassette can be varied depending on the application. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. (Herrara-Estrella et al., 1983). Viral promoters include the 35S and 19S RNA promoters of cauliflower mosaic virus. (Odell et al. 1985). Possible plant promoters include the ribulose-1,3-bisphosphate carboxylase small subunit promoter and the phaseolin promoter.

A promoter which is expressed concurrently with or prior to the normal activation of the homologous endogenous sequence is generally preferred. A constitutive promoter is most preferred, such as the cauliflower mosaic virus promoter. This promoter is constitutive because its operation is relatively independent of the developmental stage of the cell in which it is contained.

A regulated or inducible promoter, such as ones associated with the ribulose-1,5-bisphosphate carboxylase, the chlorophyll binding proteins or the glycine-rich root protein genes are also suitable. Control may be either temporal with respect to the developmental stage of the cell, or spatial with respect to different parts or organs of the plant. The operation of a promoter may also vary depending on its location in the genome. Thus, an inducible promoter may become fully or partially constitutive in certain locations. Promoters particularly useful in the present invention include tuber specific promoters such as the promoter for the gene encoding the tuber protein patatin. Notably, in situations wherein the DAPP1-silencing is stronger, some plants could possibly become sick due to strong constitutive activation of the defense system. Thus it will be may beneficial to include (pathogen) inducible promoters for producing disease-resistant plants via DAPP1-silencing without affecting plant overall fitness too much.

In addition to a promoter sequence, the expression cassette may include a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. (Alber and Kawasaki, 1982). Polyadenylation sequences include, but are not limited to the Agrobacterium octopine synthase signal (Gielen et al., 1984) or the nopaline synthase signal (Depicker et al., 1982).

The vector may also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

Other features of the vectors of the present invention include various 5' untranslated leader sequences such as the "cab leader" from petunia or the "omega leader" from tobacco mosaic virus.

In the present invention the polynucleotide sequence to be introduced using the vectors described above is a "polynucleotide sequence from a gene encoding a protein associated with phophotase activity (DAPP1)." This term as defined here refers to a sub-sequence or full length polynucleotide sequence of the DAPP1 gene which, when present in a transgenic plant has the desired effect, of inhibiting expression of the endogenous UGPase gene. In the case of both expression of transgenes and inhibition of endogenous genes (e.g., by antisense, ribozymes or sense suppression) one of skill will recognize that the inserted polynucleotide sequence need not be perfectly identical and may be "substantially identical" to a sequence of the gene from which it was derived.

In the case of polynucleotides used to inhibit expression of an endogenous gene, the introduced sequence also need not be perfectly identical to a sequence of the target. The introduced polynucleotide sequence will typically be at least substantially identical to the target endogenous sequence.

The introduced sequence also need not be full length relative to either the primary transcription product or fully processed mRNA. A higher sequence identity in a shorter than full length sequence compensates for a longer less identical sequence. Furthermore, the introduced sequence need not have the same intron or exon pattern, and identity of non-coding segments will be equally effective. Normally, a sequence of between about 10 nucleotides and 2000 nucleotides should be used, though a sequence of between about 100 and about 1500 nucleotides is preferred or a full length gene is especially preferred.

Two nucleic acid sequences or polypeptides are said to be "identical" if the sequence of nucleotides or amino acid residues in the two sequences is the same when aligned for maximum correspondence as described below. Optimal alignment of sequences for comparison may be conducted by a local homology algorithm (Smith and Waterman, 1981), by the homology alignment algorithm (Needleman and Wunsch, 1970), by the search for similarity method (Pearson and Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), BLAST available from NCBI or by inspection. These references are incorporated herein by reference.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

Transcription of the Desired Polynucleotide Sequence in Plant Cells

The vectors described above can be microinjected directly into plant cells by use of micropipettes to mechanically transfer the recombinant DNA. (Crossway, 1985). The genetic material may also be transferred into the plant cell using polyethylene glycol (Krens, et al., 1982).

Another method of introduction of polynucleotide sequences is particle acceleration of small particles with the nucleic acid either within the matrix of small beads or particles, or on the surface (Klein, et al., 1987). Yet another method of introduction is fusion of protoplasts with other entities, such as, minicells, cells, lysosomes or other fusible lipid-surfaced bodies. (Fraley et al., 1982). The DNA may also be introduced into the plant cells by electroporation (Fromm et al., 1985). In this technique, plant protoplasts are electroporated in the presence of plasmids containing the expression cassette. Electrical impulses of high field strength reversibly permeabilize biomembranes allowing the introduction of the plasmids.

Cauliflower mosaic virus (CaMV) may be used as a vector for introducing the anti-sense DNA into plant cells. (Hohn et al., 1982; U.S. Pat. No. 4,407,956). In accordance with the described method, the entire CaMV vial DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

A preferred method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Preferred *Agrobacterium* strains useful in the present invention include LBA 4404, C58C1, EHA 101, W2/73, R1601, LBA 288, GV 3850, A281, GV311 SE, A856, A136, GC3101, 1S955, and bo 42.

*Agrobacterium* is a genus in the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, J., 1987).

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid, such vectors are typically termed binary vectors. (Hoekema et al., 1983). The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkun and Ausubel, 1981), promoters, (Lawton et al., 1987) and structural genes for antibiotic resistance as a selection factor (Fraley et al., 1983).

All plant cells which can be transformed by *Agrobacterium* and from which whole plants can be regenerated can be transformed according to the present invention to produce transformed intact plants which contain the desired DNA. There are two common ways to transform plant cells with *Agrobacterium*:

(1) co-cultivation of *Agrobacterium* with cultured isolated protoplasts, or
(2) transformation of intact cells or tissues with *Agrobacterium*.

Most dicot species can be transformed by *Agrobacterium*. All species which are a natural plant host for *Agrobacterium* are transformable in vitro.

After transformation, transformed plant cells or plants comprising the introduced DNA must be identified. A selectable marker, such as those discussed, supra, is typically used. Transformed plant cells can be selected by growing the cells on growth medium containing the appropriate antibiotic. The presence of opines can also be used if the plants are transformed with *Agrobacterium*.

After selecting the transformed cells, one can confirm expression or lack of expression of the relevant gene. Simple detection of the levels of mRNA can be achieved by well known methods in the art, such as Northern blot hybridization.

After determination that the inserted nucleotide sequence has affected the plant cell, whole plant regeneration may be desired. All plants from which protoplasts can be isolated and cultured to give whole regenerated plants can be hosts for the polynucleotide sequences of the present invention. Some suitable plants may include, but is not limited to, *Arabidopsis, Brassica, Raphanus, Sinapis, Atropa, Capsicum, Hyoscyamus, Lycopersicon, Nicotiana, Solanum, Oryza, Petunia, Digitalis, Majorana, Cichorium, Helianthus, Lactuca, Bromus, Antirrhinum, Hererocallis, Nemesia, Pelargonium,*

*Panicum, Pennisetum, Ranunculus, Senecio, Salpiglossis, Cucumis, Browaalia, Glycine, Lolium, Zea, Triticum, Sorghum, Malus, Apium, Phaseolus, Pisum, Hordeum, Beta* and *Datura.*

Plant regeneration from cultured protoplasts is described in (Evans et al., 1983); and (Vasil I. R. ed., Vol. I, 1984, and Vol. III, 1986. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytolcinins. Efficient regeneration will depend on the medium, on the genotype, and on the history of the culture. If these three variables are controlled, then regeneration is usually reproducible and repeatable. Regenerated plants with the desired characteristics are typically identified by determining activity of the target gene or expressed protein.

Finally, one of skill will recognize that after the expression cassette is stably incorporated in transgenic plants and confirmed to be operable, it can be introduced into other plants by sexual crossing. Any of a number of standard breeding techniques can be used, depending upon the species to be crossed.

The Invention

Protein phosphorylation and dephosphorylation processes are believed to play a role in signal transduction of disease resistance controlled by R genes. To understand how the broad-spectrum R gene RPW8 (Xiao et al., 2001) activates defense response against powdery mildew, a screen for RPW8-interacting partners was performed using the yeast two hybrid system. A protein phosphatase gene (SEQ ID NO. 1 (At1g22280)) was identified as a potential RPW8-interacting gene. A gene with a full-length cDNA comprises six exons and five introns and is predicted to encode a protein phosphatase type 2C (SEQ ID NO. 2 (AAM91671)). FIG. 1 shows the schematic structure of the At1g22280 gene (A) and its predicted protein (B). At1g22280 contains 6 exons (represented by shaded boxes with the coding regions in dark gray) and 5 introns (lines). Arrows indicate the position of the translational start and stop. The predicted protein (AAM91671) has 281 amino acids with a molecular weight of 30721.7 daltons. It contains a C-terminal PP2C catalytic domain.

Figure 2:
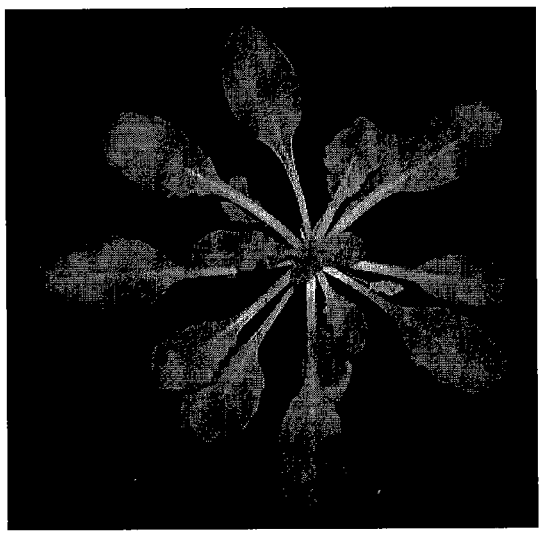
FIG. 2 shows that down-regulation of DAPP1 results in spontaneous HR-like cell death.
Figure 2:
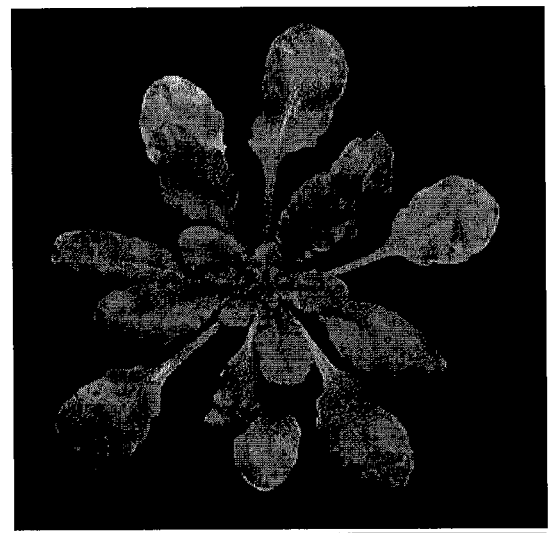
Figure 2:
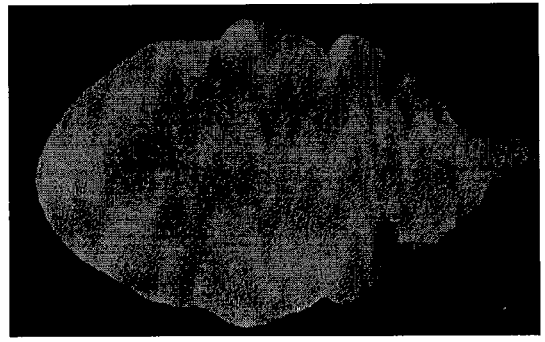
Figure 2:
Figure 3:
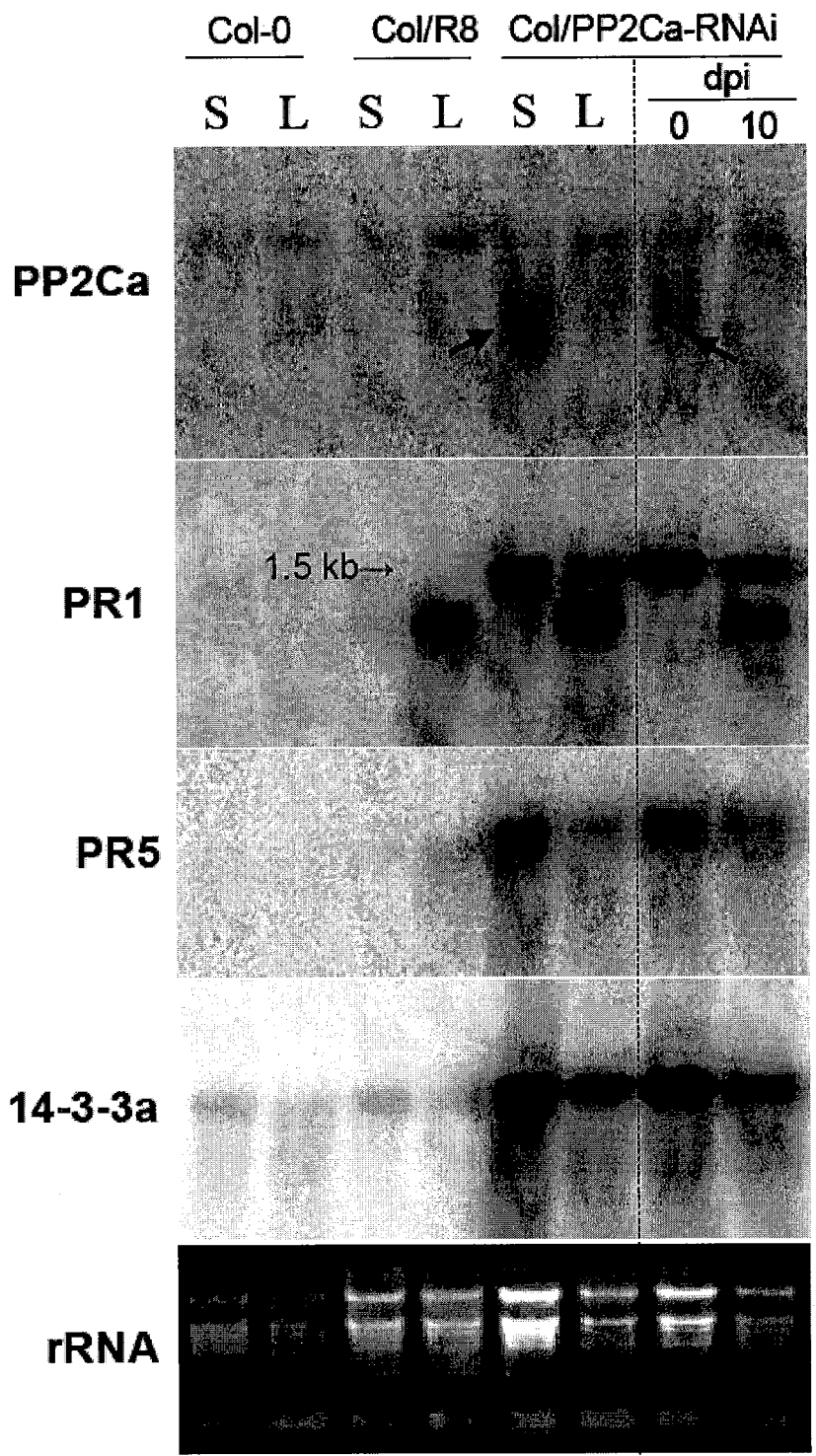
FIG. 3 shows that down-regulation of DAPP1 results in constitutive expression of defense-related genes.

The present inventors are unaware of any prior knowledge linking this named gene DAPP1 to increasing disease resistance in plants. The present invention is based on these findings and that silencing this protein phosphatase gene by an interfering nucleotide sequence results in HR-like cell death and constitutive expression of defense-related genes as shown in FIGS. 2 and 3. The specificity of silencing was supported by the observation that expression of the most closely related PP2C gene was not affected and thus the gene encoded by SEQ ID NO. 1 was named the "defense-associated protein phosphatase type 2C one" (DAPP1), as described above.

Figure 5:
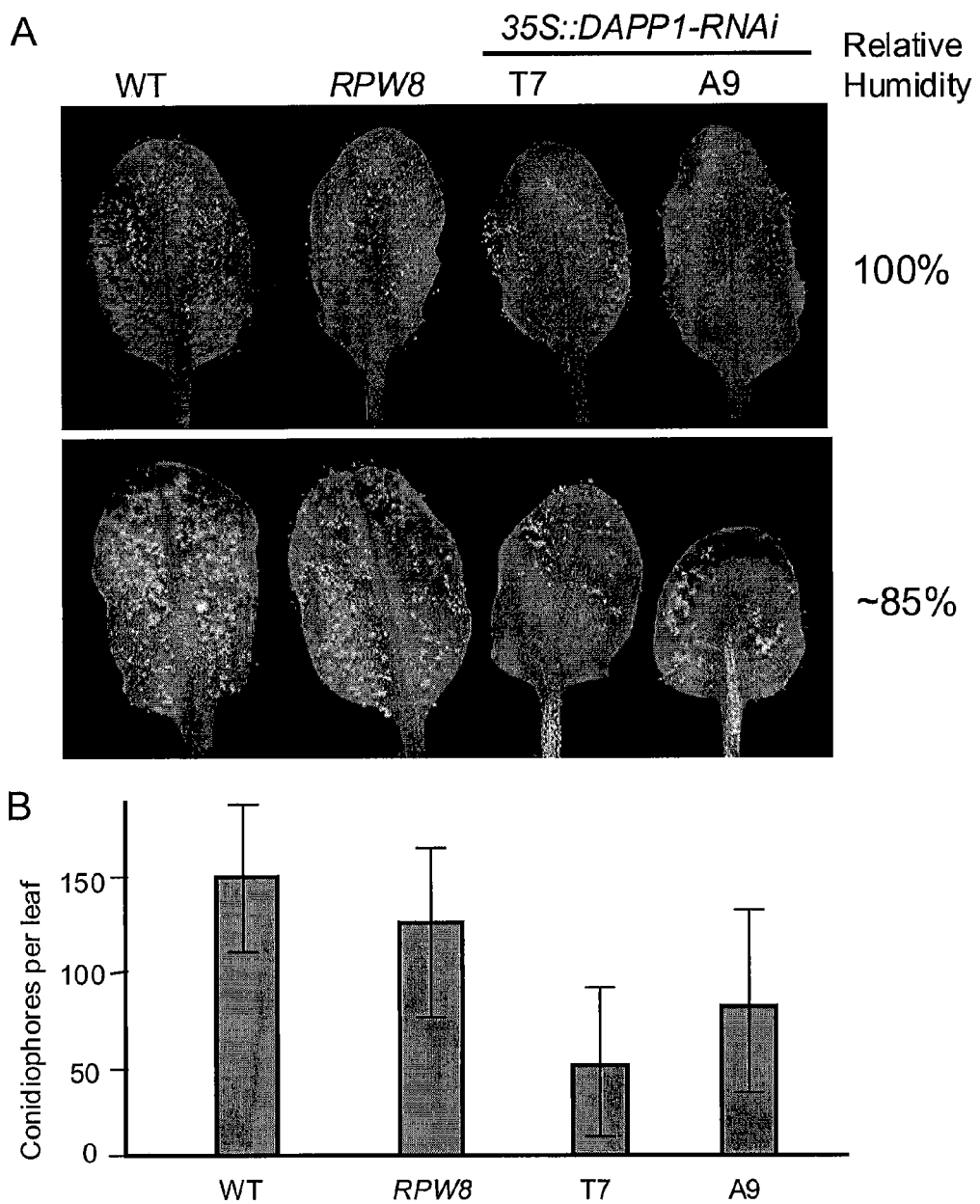
FIG. 5 shows that down-regulation of DAPP1 leads to enhanced resistance to downy mildew (A) at different levels of humidity; (B) the number of conidiophores on the lower side of infected leaves.
Figure 6:
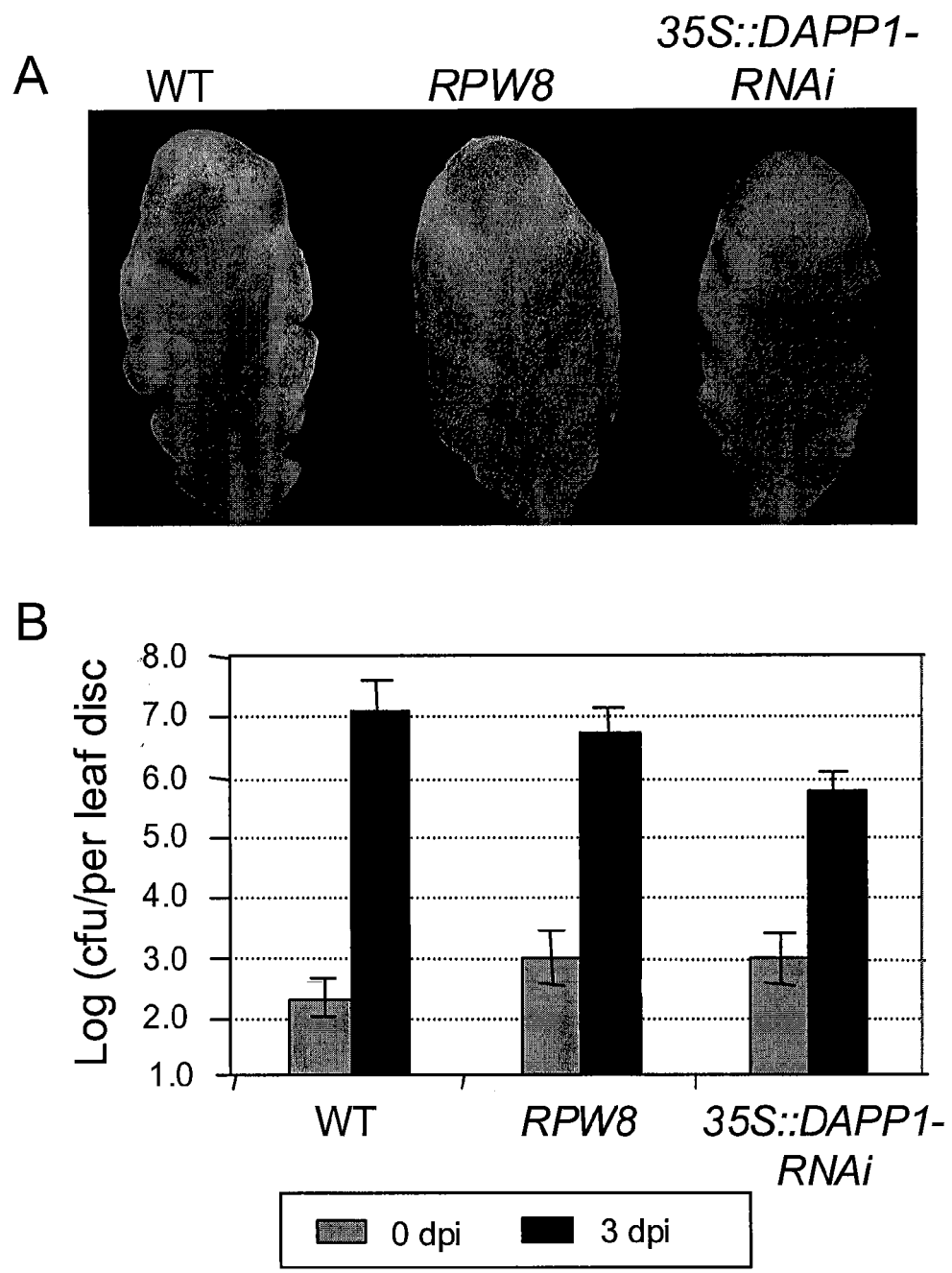
FIG. 6 shows that the down-regulation of DAPP1 leads to enhanced resistance to *Pseudomonas* (A) different genotype leaves (B) level of bacterial growth from each genotype.

Importantly, *Arabidopsis* plants, with reduced DAPP1 mRNA levels, exhibited enhanced disease resistance against multiple pathogens including virulent bacteria strains of *Erysiphe cichoracearum* (FIG. 4), *Peronospora parasitica* (FIG. 5) and *Pseudomonas syringae* (FIG. 6).

Genetic analysis indicated that DAPP1 negatively regulates a defense pathway that requires signaling components salicylic acid, PAD4 and EDS5 (FIG. 7), which is theorized to be the same pathway used by RPW8 and some other R genes, such as those encoding a nucleotide-binding site and leucine-rich-repeat (NB-LRR) (Van der Biezen et al., 2000).

It has also been confirmed that the DAPP1 protein tagged with hemagglutinin (HA) is a biologically active phosphatase. Furthermore, by using agrobacterium-mediated transient expression in tobacco leaves, it has been found that the HA-DAPP1 inhibits RPW8-dependent degradation of a putative protein complex containing a 14-3-3 (named 14-3-3a) which is another putative RPW8-interacting protein identified in the yeast two hybrid system. In addition, plants with reduced DAPP1 expression had strong induction of the 14-3-3a gene, suggesting that DAPP1 negatively regulate 14-3-3a at the transcriptional level.

The present invention provides a plant with a genetic modification resulting in reduction or elimination of the functionality of DAPP1 or a DAPP1 homolog. Reduction in functionality of DAPP1 or a DAPP1 homolog was measured relative to a control plant not having the genetic modification.

As discussed above, any means for reduction in functionality of a protein product can be employed to reduce or eliminate DAPP1 functionality, such as means which result in the absence or alteration of genetic code in the plant species required for expression of an intact, active DAPP1 or DAPP1 homolog product. For example, the plant may include a genetic modification comprising a mutation in a gene coding for DAPP1 or a DAPP1 homolog. Alternatively, the plant may include a genetic modification comprising a interfering nucleotide sequence encoding an antisense or a small interfering RNA (siRNA) complimentary to DAPP1 or a DAPP1 homolog. In a preferred embodiment, the genetic modification involves gene silencing of DAPP1 or a DAPP1 homolog. Silencing DAPP1 with an appropriate inducible promoter would be expected to lead to activation of resistance against different types of pathogens, which is more desirable in the absence of the cognate R genes. A dominant negative mutation in DAPP1 is also an attractive option. The genetic modification may be chromosomal or extrachromosomal, depending on the particular strategy selected. Multiple genetic modifications may be involved, e.g., a combination of two or more of the foregoing strategies.

Plants in which the present invention will be useful include all plants ordinarily having an *Arabidopsis thaliana* DAPP1 homolog(s). AtDAPP1 homologs are known to exist in a variety of plant species of economic importance. For example, one EST clone (BG544163) from *Brassica rapa* shows 88% nucleotide sequence identity to DAPP1 and a rice PP2C gene (OsJN00048) shows 65% amino acid sequence identity and 77% sequence similarity to DAPP1. Preferred plant species are *Brassica*, rice, tomato, and maize. For example, the plant may include, but is not limited to:

a *Brassica* species, such as *B. rapa, B. oleracea*, and *B. napus*;
a *Lycopersicon* species, such as *L. esculentum*;
an *Oryza* species, such as *O. sativa* L. and *O. glaberrima*;
a *Zea* species, such as *Z. mays, Z. tunicata, Z. everata, Z. indurata, Z. indentata, Z. saccharata, Z. ceritina*; and
a hybrid of any of the foregoing.

The invention also includes plant matter (such as seeds, fruits or other plant matter) harvested from a plant of the invention, packages and/or containers comprising such vegetable matter, and economic transactions involving exchanges of such vegetable matter.

The plants of the invention exhibit increased pathogen resistance relative to resistance of a corresponding control plant which is genetically identical to the plant of the invention with the exception that the control plant does not have the genetic modification of the plant of the invention. The increased pathogen resistance may, for example, include increased resistance to a bacterial or fungal pathogen. Specifically, the increased resistance may include resistance to:

an *Erysiphe* species, such as *E. cichoracearum; E. orontii; E. lycopersicii; E. cruciferarum;* a *Peronospora* species, such as *Peronospora parasitica.* a *Pseudomonas* species, such as *P. syringae.*

The invention provides methods for providing crop products (such as seeds, fruits or other plant matter) that involve the use of the modified plant species of the invention. The methods generally comprise planting, cultivating, harvesting, shipping, and/or storing such plants and/or plant products. The planting most suitably occurs in regions where non-modified plants are susceptible to any one or more of the pathogens to which the plants exhibit increased resistance. The inventions also include business methods in which plants of the invention or plant products are provided for exchange or actually exchanged in an economic transaction, such as the marketing and/or sale of such plant products.

The following examples illustrate, but do not limit, the invention.

EXAMPLES

Interaction Between RPW8 and DAPP1 in Yeast-Two-Hybrid System

There are two functional homologous genes at the RPW8 locus and they are named RPW8.1 and RPW8.2 (Xiao et al., 2001). To identify RPW8-interacting proteins, an *Arabidopsis* yeast-two-hybrid cDNA fusion library (a gift from J. D. Jones, Sainsbury Laboratory, Norwich, England) constructed based on the Matchmaker LexA two-hybrid system (CLONTECH) was screened using RPW8.2 as bait. From ~$4 \times 10^6$ cDNA clones screened, six positive clones (indicated by the activation of LacZ and LEU2 reporter genes) predicted to encode the same protein phosphatase gene (At1g22280, named DAPP1 in the text) were obtained. DAPP1 was subsequently shown to also interact with RPW8.1 in the yeast two hybrid system.

Down-Regulation of DAPP1 by RNAi in *Arabidopsis* Leads to Activation of Defenses A 5'primer (CGAATTCATGGGAAAATTTTGTTGCT-TCACT) (SEQ ID NO; 3) and a 3' primer (CGGGATCCTC-ATCTGAATCGGACCACGACA) (SEQ ID NO. 4) were used to amplify the genomic and cDNA of DAPP1 using the total genomic DNA extracted from *Arabidopsis* accession Col-0 and cDNA synthesized from total mRNA of Col-0 (Invitrogen). The PCR products were first digested with BamHI (The BamHI site is incorporated in the 3' primer) and the two products were mixed with equal amount and subject to ligation using T4 DNA ligase (Invitrogen). The ligated products were then digested with EcoRI (The EcoRI site is incorporated in the 5' primer) and subsequently ligated to the EcoRI site of a binary vector pKMB (Mylne and Botella, 1998) under control of the CaMV p35S promoter. A resultant clone carrying the genomic DNA (5' to 3') linked to the inverted cDNA (3' to 5') was identified by PCR using the 5' primer only and confirmed by sequencing. Expression of this construct generates looped double-stranded RNA molecules capable of silencing the endogenous DAPP1 by RNA interference (RNAi). The recombinant plasmid containing this construct was introduced to *Agrobacterium* strain GV3101 by electroporation. *Arabidopsis* Col-0 plants were transformed with the *Agrobacterium* strain containing the 35S::DAPP1-RNAi construct using the floral dip procedure (Clough and Bent, 1998).

Plants of Col-0 wild type (WT) and Col-0 transgenic for one copy of RPW8 under control of the native promoter, or for one copy of the 35S::DAPP1-RNAi construct were grown under short day (8 h light) for 6 weeks and then either shifted to long day (16 h light) for 1 week (indicated by "L"); or remained in short day for 1 week (indicated by "S"), or inoculated with *E. cichoracearum* UCSC1 and maintained in short day with plants shown in FIG. 2. Approximately 2 µg of total RNA was gel-blotted and probed with DAPP1, PR1, PR5 and 14-3-3a. As shown in FIG. 3, arrows indicate mRNA degradation; Dpi, days post-inoculation. Note that there were two types of PR1 transcripts induced in DAPP1-RNAi background. The bigger one is around 1.5 kb and was mainly present in plants kept in short day. The small (typical) one is around 800 bp and was induced in plants shifted in long day or infected with the powdery mildew pathogen. This experiment was repeated once with similar results.

Transgenic plants were selected by spraying Basta herbicide "Challenge" at a concentration of 0.02% (v/v) for 3 times at a 2 day-interval shortly after seed germination. Pictures were taken 1 week after shifting and shown in FIG. 2. Note HR-like lesions were seen in mature leaves of those exposed to long day. No obvious changes were observed in wild type Col-0 after shifting (not shown). This experiment was done at least three times with similar results. Among 51 independent T1 transgenic lines obtained, 15 displayed spontaneous HR-like lesions when the plants were grown in long day (16 hours light and 8 hours dark) for 3-4 weeks, FIG. 2. It was found that plants grown in short day (8 h light and 16 h dark) did not show spontaneous HR-like cell death during an observation period of 6 weeks. One line (T7) hemizygous for 35S:: DAPP1-RNAi was used to confirm the reduction/degradation of DAPP1 mRNA and expression of defence-related genes PR1 and PR5 by Northern blotting, as shown in FIG. 3. The *Arabidopsis* genome contains more than 60 PP2C genes (Kerk et al., 2002). To exclude the possibility that activation of defense responses may be caused by simultaneous silencing of DAPP1 and its close homologs, expression of the most closely related PP2C genes (At1g34750) was examined by Northern blotting. Results showed that expression of At1g34750 was not affected. Rather, it was induced to higher level in the T7 line.

Down-Regulation of DAPP1 Results in Enhanced Resistance to Pathogens

The development of spontaneous HR-like cell death and constitutive activation of defense marker genes in plants with reduced mRNA levels of DAPP1 suggested that DAPP1 may negatively regulate a plant defense pathway leading to pathogen resistance. To test this, two independent hemizygous 35S::DAPP1-RNAi lines (T7 and A9) in Col-0 background were used to test if they had enhanced disease resistance against different types of virulent pathogens. Six week-old short-day grown plants were inoculated with *Erysiphe cichoracearum* USCS1 by brushing off fungal conidia from infected *Arabidopsis* or squash leaves onto the tested plants. Inoculated plants were maintained in long day for 10 days and examined for the disease reaction (DR) phenotypes using 0-4 DR scales (0, No or very limited sporulation with HR. The fungal mycelia or conidia were barely visible to the naked eye. 1, Low level of sporulation with weaker or delayed HR. Some white powdery mildew could be seen on the tip or edge of the inoculated leaves. 2, Moderate sporulation without HR.

Figure 4:
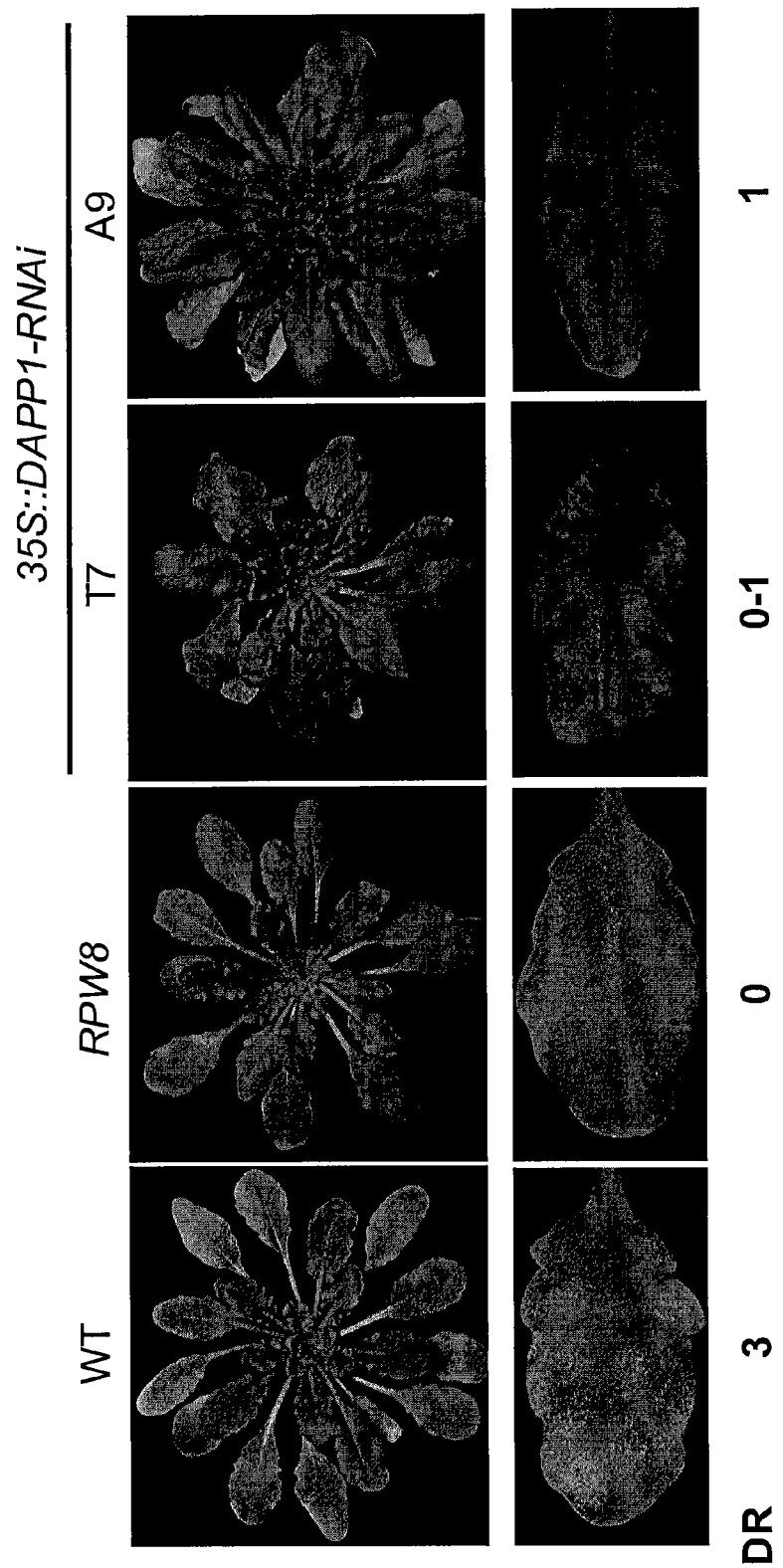
FIG. 4 shows that down-regulation of DAPP1 leads to enhanced resistance to powdery mildew.

10-30% of the leaf surface was covered by powdery mildew. 3, Heavy sporulation without HR. 30-60% of the leaf surface was covered by powdery mildew. 4, Very heavy sporulation without HR. >60% of the leaf surface was covered by powdery mildew). As shown in FIG. 4, the two 3 S::DAPP1-RNAi lines were resistant (0-1) or moderately resistant (1) to the powdery mildew isolate, while wild type Col-0 plants were fully susceptible (3-4).

To test whether the resistance of the silenced lines depends on long day conditions, inoculated plants were kept in short day and it was found that the two silencing lines still had enhance resistance to the pathogen, even though the degree of resistance was slightly lower (1-2) (data not shown). Plants (~20 plants for each genotype) were grown under short day (8 h light) for 4 weeks and then inoculated with *P. parasitica* Noco2 by spraying 4×104 *Peronospora* conidiospores/mL water suspension conditions and kept in long day under different relative humidity (RH) (100% or ~85%). The plants were examined and photographed at 5.5 dpi. A typical infected leaf from each genotype was presented as shown in FIG. 5A. For the plants kept under ~85% RH, the number of conidiophores on the lower side of infected leaves was counted with the aid of a dissecting microscope with values set forth in FIG. 5B. Note that under 100% RH conditions, both sides of the leaves had conidiophores, whereas under ~85% RH conditions, there were no or very few conidiophores on the upper side of the leaves of all plants, but there were plenty of conidiophores on the lower side of the same leaves. Thus, under ~85% RH conditions, the two 35S::DAPP1-RNAi lines were significantly less susceptible to the pathogen compared with Col-0 wild type plants (P<0.0001).

Resistance of the DAPP1-silenced plants to a virulent bacterial pathogen was also tested. Seven week-old plants (5 weeks in short day and then two weeks in long day) were inoculated with *Pseudomonas syringae* pv maculicola strains 4326 by infiltration of a bacterial suspension ($OD_{600}$=0.0002) into mature leaves with a syringe. At 3 dpi, plants were examined by the naked eyes and photographed. One typical leaf from each genotype was presented as shown in FIG. 6A. The bacterial growth was measured by quantification of the number of bacteria in 10 leaf discs (5 mm in diameter) from each genotype at 0 dpi (grey bars in FIG. 6B) and 3 dpi (black bars in FIG. 6B). This experiment was repeated once with similar results. The tested 35S::DAPP1 line T7 had clear enhanced resistance compared with Col-0 wild type plants, with a bacterial growth at least 10 magnitudes lower than Col-0.

DAPP1 Negatively Regulates a Salicylic Acid-Dependent Defense Pathway

Figure 7:
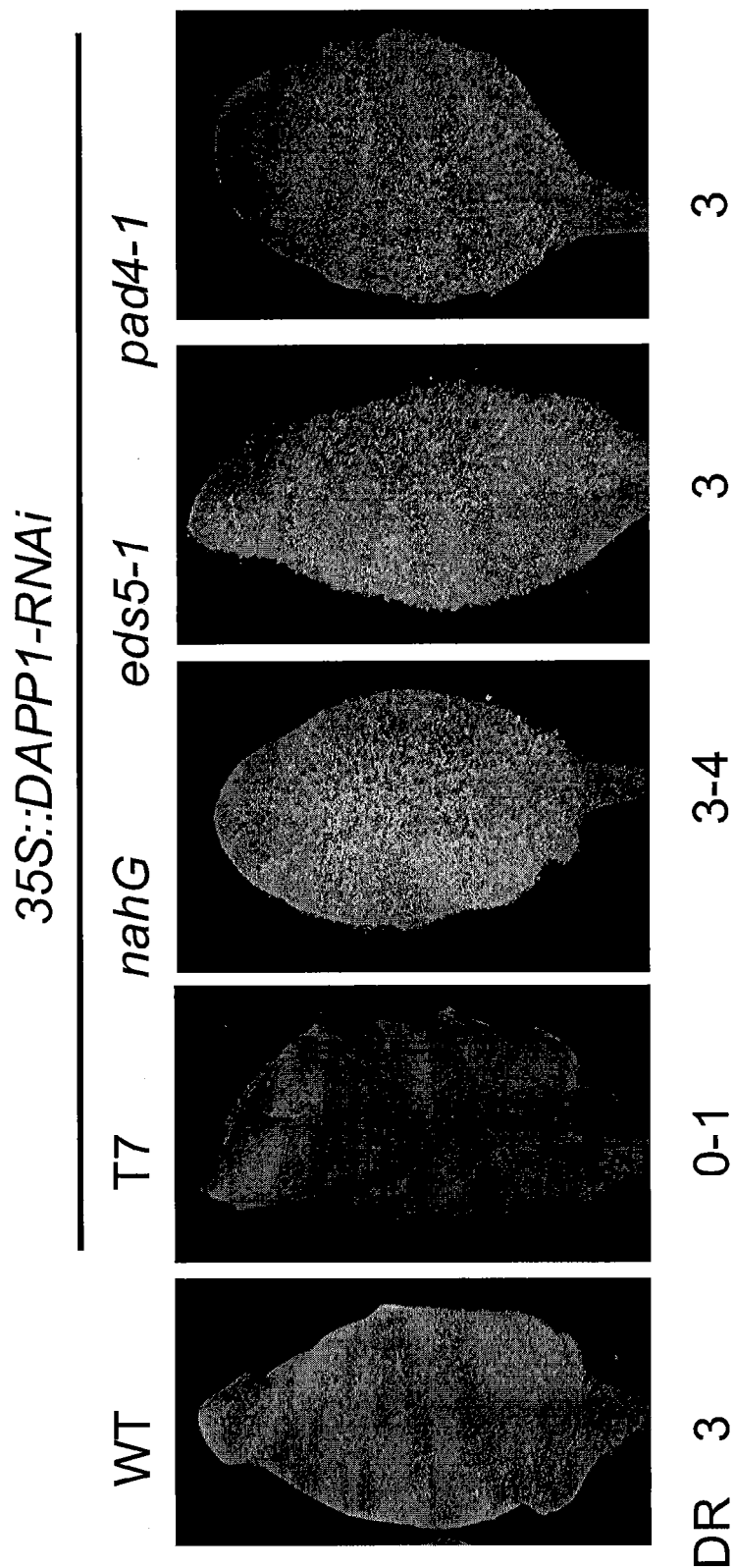
FIG. 7 shows that DAPP1 negatively regulates a salicylic acid-dependent defense pathway.

To determine what defense pathway DAPP1 may negatively regulate, the 35S::DAPP1-RNAi transgene in transgenic line T7 was introduced, by crossing, to genetic backgrounds in which the salicyclic acid (SA)-dependent pathway used by RPW8 and some NB-LRR R genes is impaired. Specifically, T7 was crossed to Col-0 transgenic for NahG, a bacterial gene whose product depletes SA. One typical leaf for each genotype is shown in FIG. 7. Numbers underneath the leaf pictures indicate the degree of resistance/susceptibility. F2 individuals containing 35S::DAPP1-RNAi (selected by spraying basta herbicide) and NahG (identified by PCR) did not show any sign of spontaneous cell death and were fully susceptible to *E. cichoracearum* UCSC1. Similarly, F2 individuals containing the 35S::DAPP1-RNAi transgene and pad4-1 (PAD4 encodes a lipase-like protein required for function of the R genes mentioned above; (Jirage et al., 1999) or eds5-1 (EDS5 encodes a MATE family transporter also required for R gene function; (Nawrath et al., Plant Cell 14, 275-286) were generated, identified, and tested against *E. cichoracearum* UCSC1. Those plants had no spontaneous cell death and were also as susceptible as Col-0 wild type plants. These results together suggested that DAPP1 negatively regulates an SA-, PAD4- and EDS5-dependent defense pathway that is probably the same pathway used by RPW8 and some NB-LRR R genes (Van der Biezen et al., 2000).

DAPP1 is a Biologically Active Phosphatase

Figure 8:
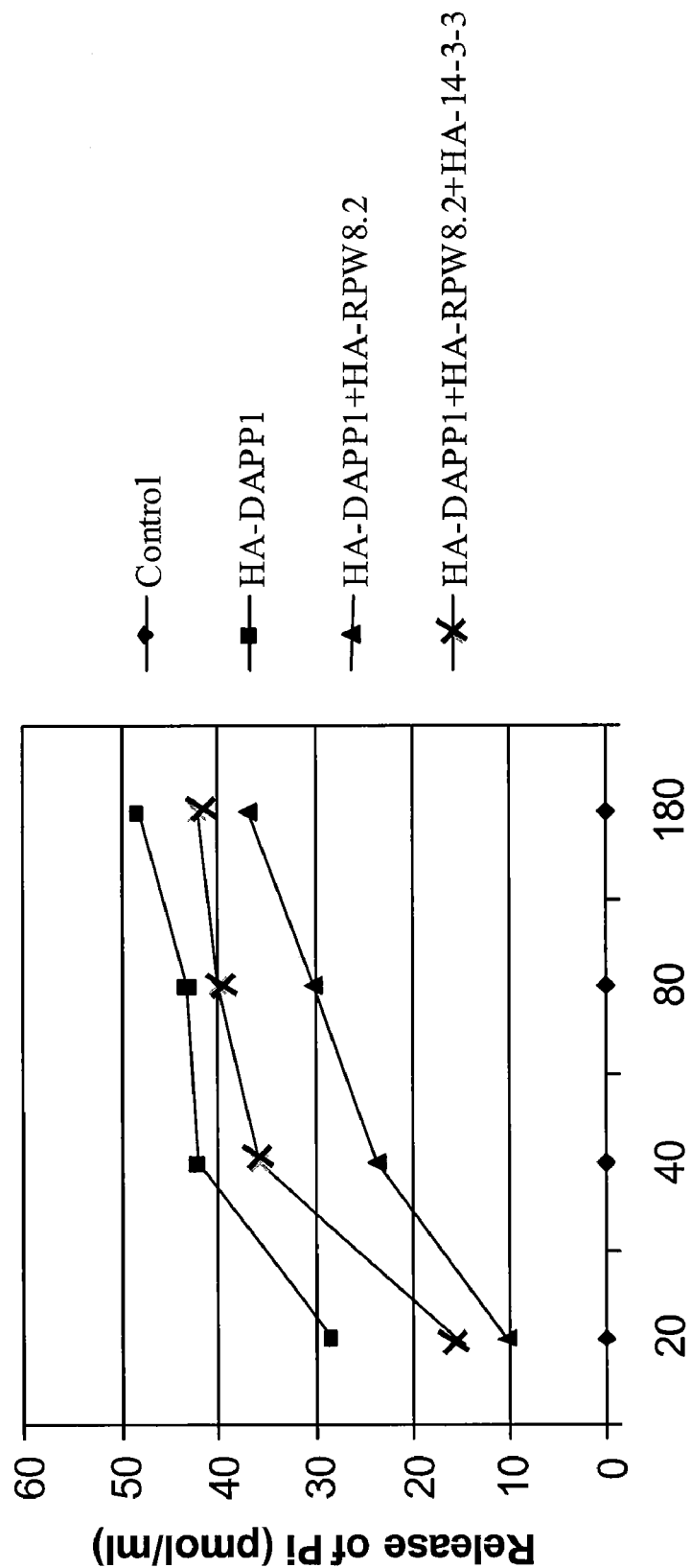
FIG. 8 shows that DAPP1 is a biologically active protein phosphatase.

The cDNA of DAPP1 without the ATG start codon was cloned in the BamHI and EcoRI site of pPILY that contains an intron-tagged hemagglutinin (HA) (Ferrando et al., 2000). The resultant 35S::HA-DAPP1 cassette was released by XhoI and SacI digestion and cloned into binary vector pSLJ755I5. The construct was then introduced to *Agrobacterium* strain GV3101. The 35S::HA-DAPP1 construct was transiently expressed in *Nicotiana benthamiana* or *N. tabacum* leaves by Agroinfiltration (Peart et al., 2002). At 48 hours after infiltration, total protein extracted from 2 g of infiltrated leaf tissue was used to immunoprecipitate the HA-DAPP1 recombinant protein using Anti-HA coupled matrix slurring (Roche). Proteins extracted from infiltrated leaves at 48 hours after infiltration were immunoprecipitated by anti-HA antibody and ~50 ng purified protein was incubated with 32P-labeled Casein at 30° C. for up to 180 minutes. Phosphatase activity of the purified HA-DAPP1 recombinant protein was measured as the amount of 32Pi in picomole released from 32P-labeled Casein at 20, 40, 80 and 180 minutes after incubation (Bertauche et al. 1996; MacKintosh, 1993). Values presented in FIG. 8 have been subtracted by the amount of 32Pi released in control samples that contained buffer only. The purified HA-DAPP1 recombinant protein extracted from agroinfiltrated tobacco leaves was able to dephosphorylate the $^{32}P$ labeled casein substrate, indicating DAPP1 is a biologically active phosphatase.

HA-DAPP1 Stabilizes a Protein Complex Containing a 14-3-3 in Tobacco

Figure 9:
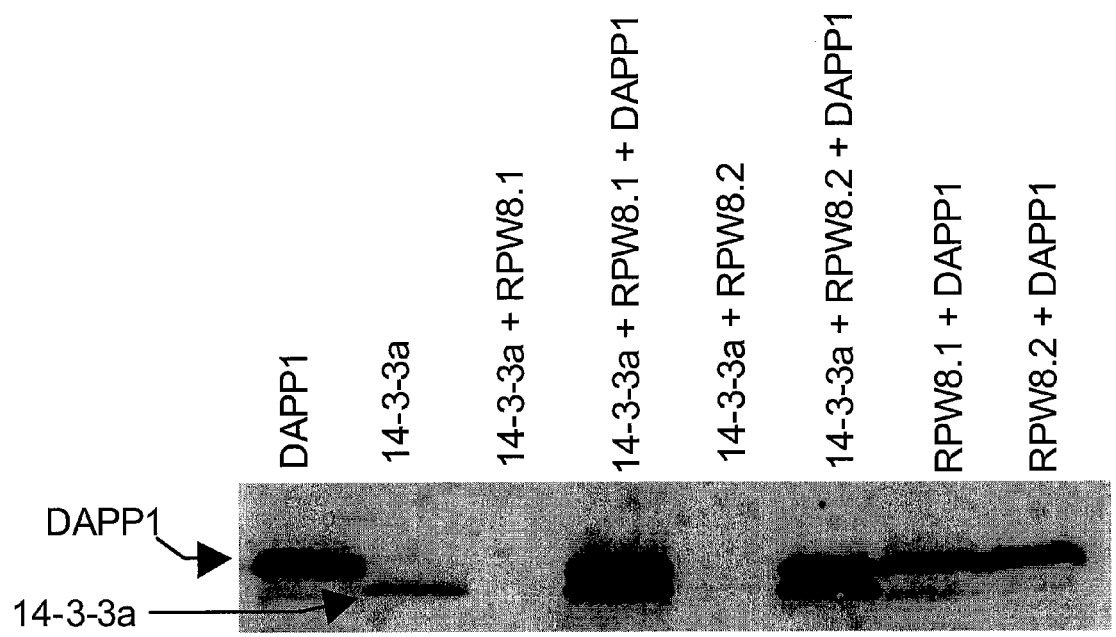
FIG. 9 shows that DAPP1 stabilizes a putative protein complex containing a 14-3-3.

Transient expression of both RPW8.1 and RPW8.2 under control of the native promoters in tobacco induces cell death (Peart et al., PNAS, 99: 10865-10869), suggesting that the RPW8 signaling pathway is conserved between *Arabidopsis* and tobacco. To test if RPW8 interacts with 14-3-3a in vivo, epitope-tagged RPW8 and 14-3-3a were constructed. Specifically, RPW8.2 cDNA and 14-3-3a cDNA were separately in-frame fused with HA in the same way as for HA-DAPP1 described in above. RPW8.1 genomic DNA was translationally fused with 3×myc at the carboxyl-terminus. These constructs were introduced to *Agrobacterium* strain GV3101. Agrobacterial cells containing each of the constructs were then infiltrated into leaves of 6 week-old *N. benthamiana* plants alone or together (all adjusted to a concentration of $OD_{600}$=0.2). At 48 hours after infiltration, total proteins were extracted from ~200 mg infiltrated leaf tissue and ~5 µg of total proteins was used for Western blotting assay with anti-HA antibody. Co-transient expression of RPW8 with 14-3-3a in tobacco results in disappearance of 14-3-3a, as shown in FIG. 9, even though HA-RPW8.2 or RPW8-myc recombinant proteins were not detectable. Significantly, co-transient expression of HA-DAPP1 together with HA-14-3-3a and HA-RPW8.2 or RPW8.1-myc resulted in stabilization of HA-14-3-3a, as shown in FIG. 9. These results suggested that expression of RPW8.1 or RPW8.2 trigger degradation of 14-3-3a and that DAPP1 may inhibits this process by dephosphorylating RPW8 or 14-3-3a or both. Interestingly, it has been shown that silencing of DAPP1 resulted in a strong induction of 14-3-3a, indicating that regulation of 14-3-3a by DAPP1 also operates at the transcription level.

Rapid Induction of DAPP1 by Inoculation of Bacterial Pathogens

Figure 10:
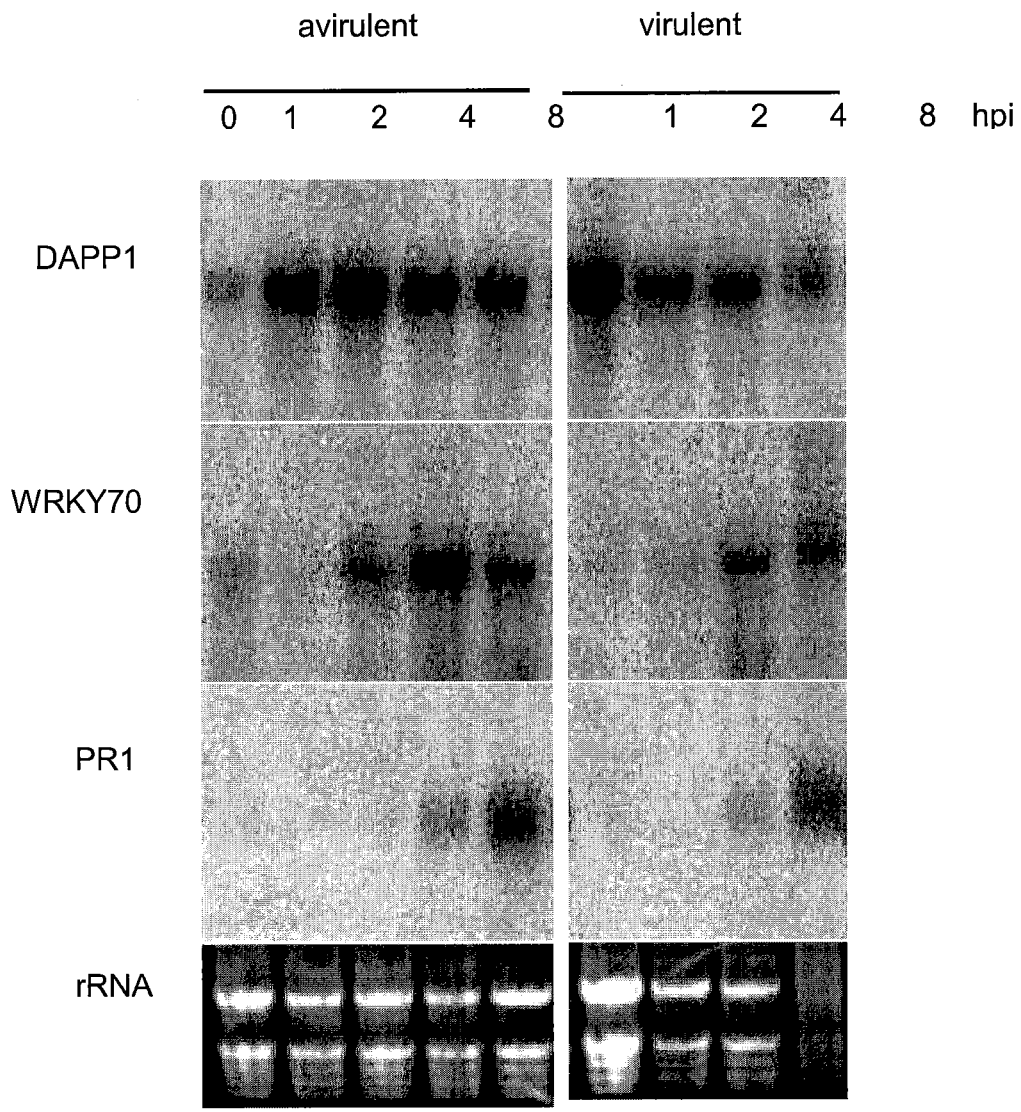
FIG. 10 shows the rapid induction of DAPP1 by avirulent and virulent bacterial pathogen.

To see if DAPP1 expression is pathogen-responsive, leaves of 5 week-old Col-0 plants were infiltrated with bacterial cells (OD600=0.0002) of a *P. syringae* EM4326 strain containing AvrRpm1 or an empty vector. Total RNA was extracted from uninoculated leaves and inoculated leaves at 1, 2, 4, and 8 hour post-inoculation (hpi), gel blotted and probed with DAPP1, WRKY70, and PR1 sequentially. Amount of RNA loaded was reflected by rRNA. DAPP1 is induced by both strains as early as an hour after infiltration of bacterial cells, which was earlier than the induction of WRKY70 (2-4 hpi), a transcription factor, and PR1 (4-8 hpi), as shown in FIG. 10, both of which have been demonstrated to be rapidly induced by pathogens. However, it can not be ruled out that wounding caused by infiltration may also induce DAPP1 expression.

Co-Suppression of DAPP1 Enhances RPW8-Mediated Cell Death

Figure 11:
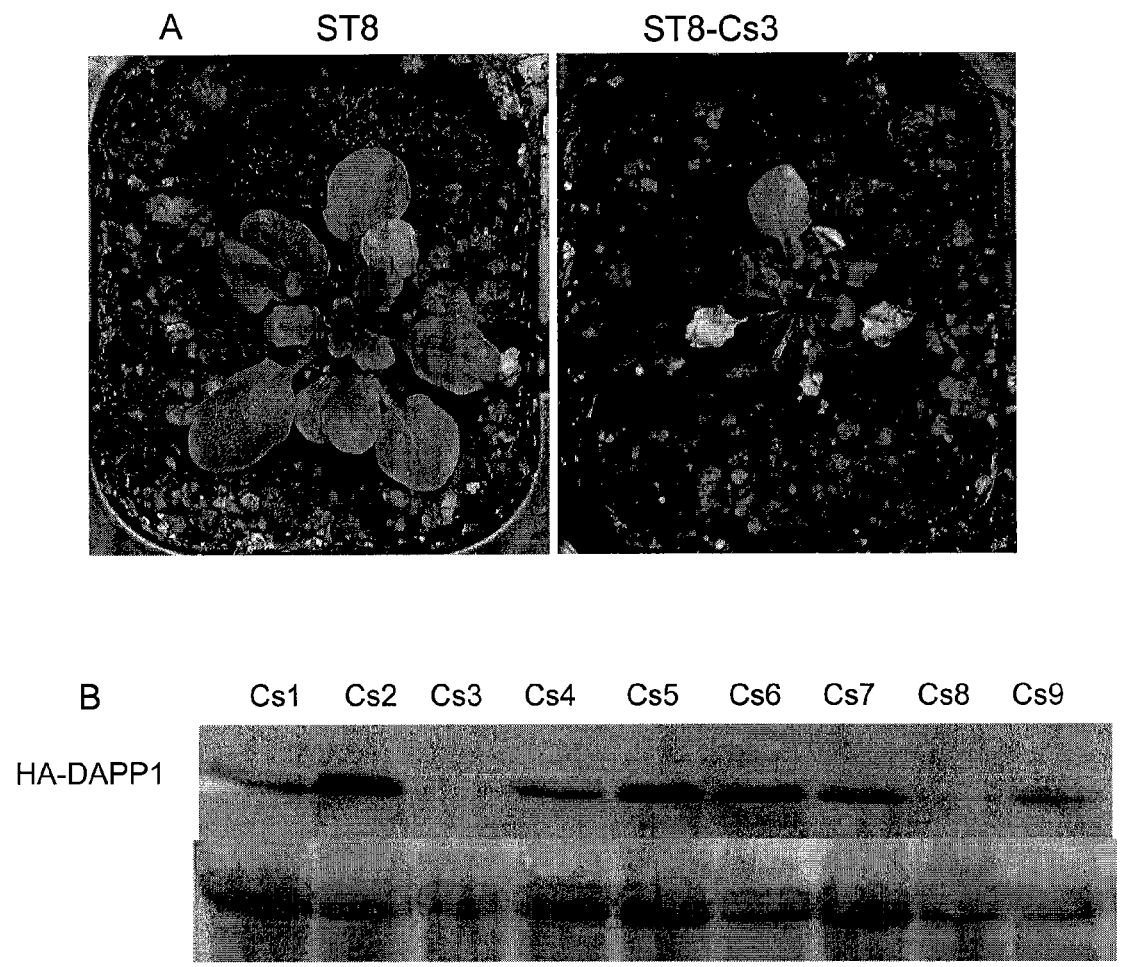
FIG. 11 shows that co-suppression of DAPP1 in RPW8 backgrounds results in enhanced cell death.

To see if over expression of DAPP1 affects RPW8's function, the 35S::HA-DAPP1 construct was introduced into a Col-0 line transgenic for RPW8 (ST8) by agrobacterium-mediated transformation. In particular, referring to FIG. 11A, a Col-0 transgenic line (ST8) moderately over expressing RPW8 was transformed with 35S::HA-DAPP1. ST8 plants homogeneously exhibit a low level of RPW8-mediated spontaneous HR-like cell death at ~4 weeks-old. Four (Cs3, Cs8, Cs 11, Cs14) of 15 ST8 T1 transgenic plants containing 35S::HA-DAPP1 displayed strong spontaneous cell death and reduced stature (ST8-Cs3 was shown as a representative), the remaining 11 were similar to ST8 (not shown). Referring to FIG. 11B, about 5-10 µg of total soluble proteins extracted from leaves of 4 week-old plants was gel blotted and probed with anti-HA antibody. Results from ST8-Cs10 to Cs15 were not shown. Poceau stain of the Rubisco (red bands underneath) indicated the difference in HA-DAPP1 levels was not caused by loading errors. Plants of this homozygous ST8 line moderately overexpress RPW8 and display weak spontaneous HR-like cell death phenotype at ~4 weeks old. Among 15 T1 transgenic individuals examined at age of ~4 weeks, 11 were phenotypically the same as or similar to ST8, 4 (ST8-Cs3, ST8-Cs8, ST8-Cs11, ST8-Cs14) exhibited strong spontaneous cell death and ST8-Cs3 is shown in FIG. 11A. Western blotting showed that these 4 individuals had barely detectable HA-DAPP1 (Cs3 and Cs8), whereas the rest had medium to high level of HA-DAPP1 as shown in FIG. 11B. T2 progenies derived from the 4 lines were further examined. All T2 plants containing 35S::HA-DAPP1 from ST8-Cs3 and ST8-Cs8 developed severe spontaneous cell death and had no detectable HA-DAPP1, indicating a correlation between no/low HA-DAPP1 protein expression and enhanced cell death phenotype. Importantly, the T2 plants containing 35S::HA-DAPP1 from ST8-Cs11 and ST8-Cs14 lines segregated for those having strong cell death with no HA-DAPP1 and those having a "restored" ST8 phenotype with medium to high levels of HA-DAPP1 (data not shown). These data suggest that (i) overexpression of HA-DAPP1 does not seem to suppress RPW8's function in cell death activation and (ii) probable co-suppression of the endogenous DAPP1 by HA-DAPP1 at the protein level enhances RPW8-mediated cell death. The latter is consistent with the DAPP1-silencing data and further implicates that DAPP1 acts as a negative regulator of RPW8-mediated cell death.

DAPP1 is Localized to Plasma Membrane

Figure 12:
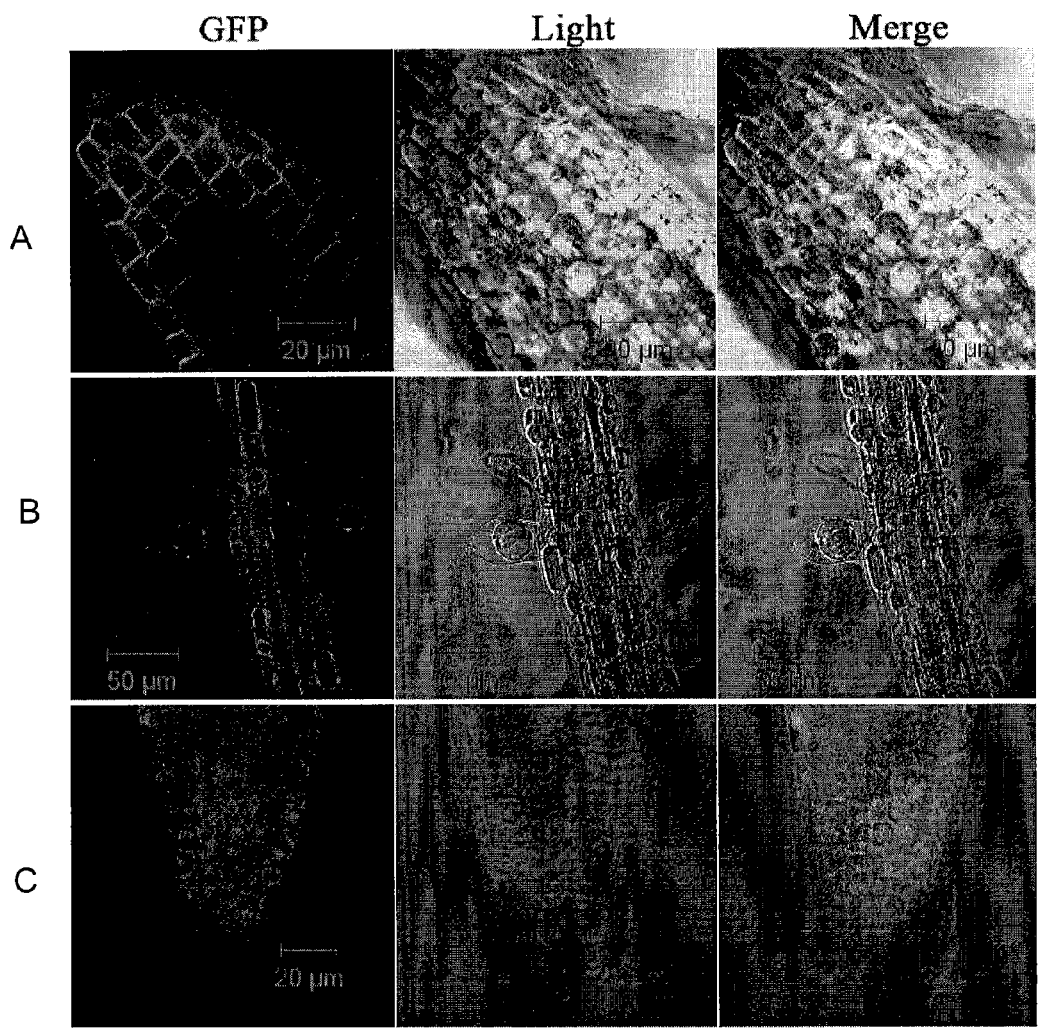
FIG. 12 shows the subcellular localization of DAPP1.

Many resistance proteins are associated with plasma membrane. To determine the subcellular localization of DAPP1, DAPP1 was in-frame fused with GFP at the 3' end and the chimeric gene was under control of a 35 S promoter. Seeds of multiple T1 Col-0 transgenic plants were sown on MS-agar medium. Root tips of 7 day-old seedlings of multiple transgenic T2 lines containing this construct were examined under a confocal microscope. GFP fluorescence observed from the 35S::DAPP1-GFP transgenic plants was mainly localized to the cell wall or plasma membrane, as shown in FIG. 12A. Plasmolysis assay in which cell plasma membrane shrinks and detaches itself from the cell wall indicated that the GFP fluorescence was from the plasma membrane, as shown in FIG. 12B. This was in contrast to the even distribution of GFP fluorescence in the cells of the root tips of the transgenic lines containing 35S::GFP, as shown in FIG. 12C. These observations suggest that the DAPP1 protein is mainly localized to the cell plasma membrane.

DAPP1 Protein Appears to be a Negative Regulator of a Global Defense Network

To determine the DAPP1-silencing effect on the whole genome transcription profile, mRNA from the T7 DAPP1-RNAi silenced lines and wild type Col-0 were hybridized to the *Arabidopsis* whole genome chip (Affymetrix, ATH1) which contains 22,500 probe sets representing about 24,000 gene sequences. Results from two independent experiments showed that over a thousand genes (1114 and 1307 in experiment I and II respectively) were up-regulated and over 500 genes (504 and 614 respectively) were down-regulated in the DAPP1-silenced line. In agreement with the Northern data set forth in FIG. 3, the defense marker genes (PR1, PR2, PR4 and PR5) for the SA pathway are induced in either both or one of the two experiments as shown below in Table 1. Unexpectedly, the defense marker genes, PDF1.2 and Thi2.2 for the jasmonic acid and ethylene pathway are also upregulated. These results suggest that DAPP1 may act as a negative regulator at a convergent step of multiple defense pathways. Interestingly, over 30 (14 in both, 12 in experiment I and 7 in experiment II) R genes or R-like genes are slightly or moderately up-regulated in the T7 line. These genes include NBS-LRRs, Cf-like and Pto-like genes (Table 1). The above speculation was also supported by the upregulation of the known defense signaling components such as EDS1, PAD3, and genes encoding MAP kinases, or WRKY transcription factors in the T7 line. Notably, two 14-3-3 genes, including 14-3-3a which interacts with RPW8 in the Y-2-H system are also up-regulated, further confirming the Northern data as set forth in FIG. 3. In addition, genes related to ethylene signaling, senescence, production of reactive oxygen species and inhibition of protein degradation are also upregulated. These results collectively indicated that down-regulation of DAPP1 has profound effect on the transcriptome of *Arabidopsis* defense network and DAPP1 acts as an essential negative regulator of a global defense networks.

TABLE 1

Genes induced in DAPP1-silenced background[a]

| Gene ID | Description | Exp I | Exp II |
|---|---|---|---|
| | 1. Disease resistance gene (R)-like | | |
| At5g36930 | similar to disease resistance protein N | 3.4 | 2.5 |
| At1g57630 | disease resistance protein RPP1-WsB | 2.3 | 9.3 |
| At4g13900 | putative disease resistance protein Hcr9-9A | 3.2 | 2.4 |
| At1g33560 | similar to disease resistance protein RPP1-WsB | 2.0 | 4.0 |
| At5g41740 | similar to disease resistance protein | 2.4 | 2.9 |
| At4g16960 | disease resistance RPP5 like protein | 2.4 | 3.2 |
| At2g32680 | putative disease resistance protein | 2.0 | 6.1 |
| At1g72940 | putative disease resistance protein | 2.0 | 7.4 |
| At2g39430 | putative disease resistance response protein | 2.0 | 2.2 |
| At2g33080 | putative LRR disease resistance protein | 2.2 | 3.3 |
| At1g66090 | similar to disease resistance protein RPP1-WsA | 2.3 | 6.1 |
| At1g72900 | similar to virus resistance protein | 2.9 | 4.6 |
| At1g72920 | similar to virus resistance protein | 2.9 | 12.3 |
| At1g13910 | putative disease resistance protein | 2.1 | 2.3 |
| At5g61560 | Pto-like resistance protein kinase | 2.3 | — |
| At4g33300 | putative NBS/LRR disease resistance protein (RFL1) | 2 | — |
| At5g58120 | resistance protein-RPP1-WsA-like | 2.2 | — |
| At4g26090 | disease resistance protein RPS2 | 2.4 | — |
| At5g44870 | disease resistance protein-like | 2 | — |
| At1g22900 | putative disease resistance response protein | 2.2 | — |
| At4g16860 | disease resistance RPP5 like protein | 2.9 | — |
| At4g16950 | disease resistance RPP5 like protein | 2 | — |
| At3g28890 | similar to disease resistance protein Cf-5 | 3.1 | — |
| At4g16880 | disease resistance RPP5 like protein | 3.1 | — |
| At4g14610 | disease resistance RPS2 like protein | 2.4 | — |
| At1g72890 | putative disease resistance protein | 2.6 | — |
| At3g24480 | putative disease resistance protein | — | 2.8 |
| At1g17600 | disease resistance protein RPP1-WsB | — | 4.0 |
| At3g25020 | putative disease resistance protein | — | 2.5 |
| At1g17610 | putative disease resistance protein | — | 2.3 |
| At5g48770 | disease resistance protein | — | 3.1 |
| At3g05370 | similar to disease resistance protein Cf-2 | — | 2.5 |
| At3g20590 | non-race specific disease resistance protein | — | 3.2 |
| | 2. Defense genes | | |
| At2g14610 | pathogenesis-related PR-1 protein | 4.9 | 41.5 |
| At2g14580 | putative pathogenesis related-1 (PR1) protein | 7.4 | — |
| At3g57260 | beta-1,3-glucanase 2 (BG2) (PR-2) | — | 8.7 |
| At3g04720 | hevein-like protein precursor (PR-4) | 2.8 | 4.7 |
| At1g75040 | thaumatin-like protein (PR-5) | — | 10.9 |
| At4g16260 | beta-1,3-glucanase class I precursor | 10.9 | 26.7 |
| At3g12500 | basic chitinase | 11.8 | 6.7 |
| At1g19610 | defensin AMP1 | 38.2 | 9.5 |
| At4g19810 | putative chitinase chitinase (EC 3.2.1.14) | 4.8 | 3.3 |
| At5g44420 | antifungal protein-like (PDF1.2) | 3.9 | 33.9 |
| At2g26020 | putative antifungal protein | 2.6 | 9.7 |
| At5g36910 | thionin Thi2.2 | 4.9 | 2.0 |
| At1g66100 | putative thionin | 17 | — |
| At2g43570 | endochitinase isolog | 5.0 | 17.0 |
| At2g35980 | similar to harpin-induced protein hin1 | 10.3 | 11.1 |
| At2g37040 | phenylalanine ammonia lyase (PAL1) | 6.5 | 5.2 |
| At1g74590 | putative glutathione S-transferase | 8.0 | 11.7 |
| At4g11650 | osmotin precursor | 29.0 | 5.2 |
| | 3. Defense-signaling genes | | |
| At3g48090 | disease resistance protein EDS1 | 2.2 | 1.9 |
| At1g33960 | AIG1 (induced by RPS2-avrRpt2 recognition) | 7.2 | 11.5 |
| At5g10520 | Pto kinase interactor (Pti1)-like protein | 2.3 | — |
| At1g54960 | NPK1-related MAPKKK | — | 2.9 |
| At1g51660 | MAP kinase kinase 4 (ATMKK4) | — | 2.9 |
| At5g13080 | WIRKY-like protein | 14.5 | 8.8 |
| At3g01970 | putative WRLKY-like transcriptional regulator protein | 7.5 | 3.8 |
| At2g38470 | putative WRKY-type DNA binding protein | 2.1 | 4.9 |
| At2g25000 | putative WRKY-type DNA binding protein | 4.5 | — |
| At5g46350 | putative WRKY-type DNA-binding protein | 3.7 | 4.5 |
| At1g79680 | similar to wall-associated kinase 2 | 6.9 | 16.9 |
| At1g18570 | myb factor | 3.5 | 3.1 |
| At3g23250 | myb-related transcription factor (binds to WRKY53) | 2.7 | 34.7 |
| At3g26830 | PAD3, (putative cytochrome P450) | 4.8 | 32.3 |
| At3g26320 | cytochrome P450 | 4.2 | 4.9 |
| At3g26210 | cytochrome P450 | 3.1 | 4.3 |
| At3g26230 | cytochrome P450 | 3.1 | 2.0 |
| At4g37370 | cytochrome P450 | 4.6 | 3.5 |
| At2g30750 | putative cytochrome P450 | 15.8 | 22.1 |

TABLE 1-continued

Genes induced in DAPP1-silenced background[a]

| Gene ID | Description | Exp I | Exp II |
|---|---|---|---|
| At2g30770 | putative cytochrome P450 | 14.4 | 12.1 |
| At5g10450 | 14-3-3 protein GF14 lambda | 4.7 | 5.2 |
| At3g02520 | 14-3-3 protein GF14 nu | 4.3 | 3.6 |
| 4. Genes involved in Redox and other signaling pathways | | | |
| At5g47230 | ethylene responsive element binding factor 5 (AtERF5) | 2.3 | 14.3 |
| At4g11280 | ACC synthase (AtACS-6) | 2.4 | 2.8 |
| At5g45890 | senescence-specific gene SAG12 | 12.1 | 11.0 |
| At5g64120 | peroxidase | 6.5 | 5.5 |
| At5g19880 | peroxidase peroxidase | 6.3 | 3.6 |
| At1g23020 | putative superoxide-generating NADPH oxidase | 5.4 | 3.2 |
| At1g26420 | similar to reticuline oxidase-like protein | 7.6 | 18.7 |
| At1g26410 | similar to reticuline oxidase-like protein | 13.2 | 5.0 |
| At4g12480 | pEARLI 1 (protease inhibitor/Lipid transfer protein) | 46.5 | 16.9 |
| At4g12500 | pEARLI 1-like protein | 21.0 | 16.2 |
| At4g12490 | pEARLI 1-like protein | 32.5 | 30.1 |
| At1g73260 | putative trypsin inhibitor | 28.1 | 4.1 |
| At2g38870 | putative protease inhibitor | 14.1 | 10.1 |
| At5g46050 | peptide transporter | 5.1 | 9.9 |
| At3g54580 | extensin precursor-like protein extensin precursor | 26.5 | 9.3 |
| At5g39670 | calcium-binding protein | 3.3 | 10.2 |
| At5g26920 | calmodulin-binding | 2.6 | 6.5 |
| At3g47480 | putative calcium-binding protein | 8.3 | 12.1 |

[a]Plants of DAPP1-RNAi T7 line and Col-0 wild type were grown under short day (8 h light), 22° C., 85% relative humidity condiitons for 6 weeks, and then shifted to long day (16 h, 22° C., 85% relative humidity conditions for 6 days. Total RNA was extracted from fully expanded leaves using TRIzol reagent and purified with Qiagene kit. Labeling of total RNA and hybridization was performed with standard procedures and the raw data were normalized andanalysed using the D-chip program. Two-fold change was used as the cutoff line. Values in the table indicate fold-of-induction of mRNA in the DAPP1-RNAi silenced line T7 in comparison with wild type.

Figure 13:
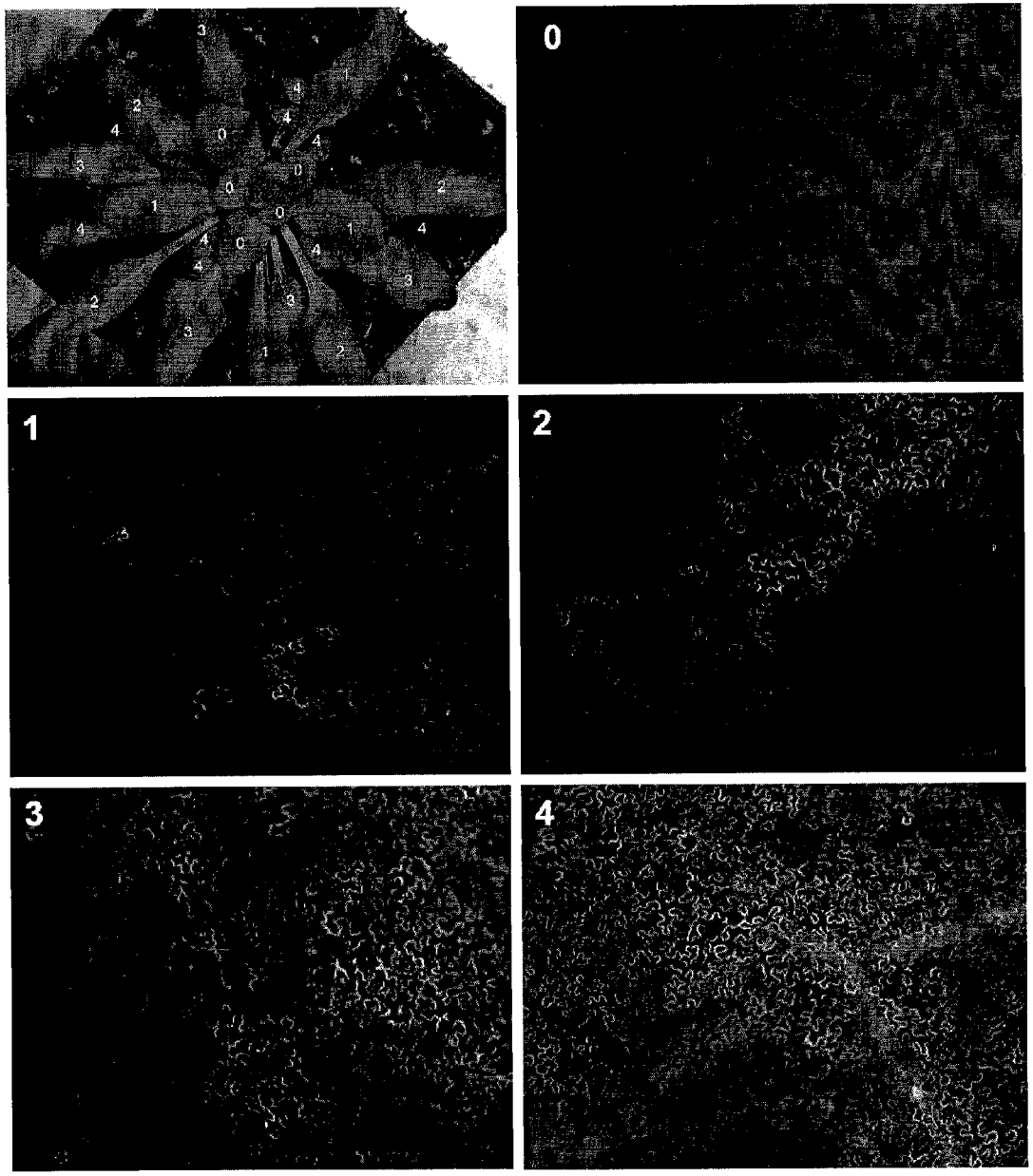
FIG. 13 shows time dependence of interaction of $YFP^N$:DAPP1 and $YFP^C$:14-3-3a. Functional fluorescent dimers were produced by fusing an amino-terminal yellow fluorescent protein (YFP) fragment to DAPP1 and a carboxyl-terminal YFP fragment to 14-3-3a. When expressed together, $YFP^N$:DAPP1 and $YFP^C$:14-3-3a produced fluorescent signals in the plasma membrane that were not seen when the subunits were expressed separately.

Using the bimolecular fluorescence complementation (BiFC) approach, it was demonstrated that DAPP1 interacts with 14-3-3a in leaves of *Arabidopsis* in vivo in an age-dependent manner. This finding implies that DAPP1 may also regulate leaf senescence via interaction with 14-3-3a. 14-3-3a is the other RPW8-interacting protein that plays a role in plant programmed cell death and resistance. FIG. 13 shows a transgenic *Arabidopsis* line expressing fusion proteins. Yellow Fluorescent Protein$^N$:DAPP1 and YFP$^C$:14-3-3a was grown in soil for 7 weeks and leaves at different developmental stages were examined for YFP fluorescence under a fluorescent microscope. YFP fluorescence indicates DAPP1-14-3-3a interaction. 0, no YFP signal; 1, <5% cells have YFP signal; 2, ~5~50% cells have YFP signal; 3, ~50~80% cells have YFP signal; 4, >80% cells have YFP signal. This result implies that DAPP1 may also regulate leaf senescence via interaction with 14-3-3a

REFERENCES

The contents of all references cited herein are hereby incorporated by reference herein for all purposes.

Alber and Kawasaki, 1982, *Mol. and Appl. Genet.*, 1:419-434.
Accession No. At1g22280.
Accession No. AAM91671.
Bertauche et al. 1996, *Eur. J. Biochem.*, 241: 193-200.
Chern et al., 2001, *Plant J.*, 27: 101-13.
Clough and Bent, 1998, *Plant J.*, 16: 735-43.
Crossway, 1985, *Mol. Gen. Genetics*, 202:179-185.
Dangl and Jones, 2001, *Nature*, 411: 826-833.
Dangl et al., 1996, *Plant Cell*, 8, 1793-1807.
Depicker et al., 1982, *Mol. and Appl. Genet.*, 1:561-573.
Evans et al., 1983, Handbook of Plant Cell Cultures, Vol. 1: (MacMillan Publishing Co., New York).
Ferrando et al., 2000, *Plant J.*, 22: 553-60.
Fraley, et al., 1982, *Proc. Natl. Acad. Sci. USA*, 79:1859-1863.
Fraley et al., 1983, *Proc. Nat. Acad. Sci. USA*, 80:4803-4807.
Fromm et al., 1985, *Proc. Natl Acad. Sci. USA*, 82:5824.
Glazebrook, 2001, *Curr. Opin Plan Bio.*, 4, 301-308.
Grant et al., 2000, *Plant J.*, 23, 441-450.
Greenberg et al., 1994, *Cell*, 77, 551-563.
Gielen et al., 1984, *EMBO J.*, 3:835-846.
Hammond-Kosack and Jones, 1997, Annual Revew of Plant Physiology and Plant Molecular Biology, 48, 575-607.
Herrara-Estrella et al., 1983, *Nature*, 303:209-213.
Hoekema, et al., 1983, *Nature*, 303:179-189.
Hohn et al., 1982 "Molecular Biology of Plant Tumors," Academic Press, New York, pp. 549-560;
Jirage et al., 1999, *Proc. Natl. Acad. Sci. U.S.A*, 96:13583-13588.
Kerk et al., 2002, *Plant Physiol.*, 129: 908-925.
Klein, et al., 1987, *Nature*, 327:70-73.
Krens, et al., 1982, *Nature*, 296:72-74.
Lamb and Dixon, 1997, *Annu. Rev. Plant Physiol Plant Mol. Biol.*, 48, 21-275.
Lam et al., 2001, *Nature*, 411, 848-853.
Lawton et al., 1987, *Plant Mol. Biol.*, 9:315-324.
Liu et al., 2002, *Plant J.*, 30: 415-429.
MacKintosh, 1993, Protein Phosphorylation: A Practical Approach, D. G. Hardie, ed. Oxford, Oxford University Press, pp 197-230.
McDowell and Dangl, 2000, *Trends Biochem Sci.*, 25, 79-82.
Mylne and Botella, 1998, *Plant Mol. Biol. Rep.*, 16, 257-262.
Morel and Dangl, 1997, *Cell Death Differ.*, 4, 671-683.
Nawrath et al., 2002, *Plant Cell*, 14, 275-286.
Needleman and Wunsch, 1970, *J. Mol. Biol.*, 48:443.
Odell et al., 1985, *Nature*, 313:810-812.
Pearson and Lipman, 1988, *Proc. Natl. Acad. Sci. U.S.A.*, 85:2444.
Peart et al., 2002, *Proc. Natl. Acad. Sci. U.S.A*, 99: 10865-10869.

Ruvkun and Ausubel, 1981, *Nature*, 298:85-88.
Sambrook et al., 1989, Molecular Cloning—A Laboratory Manual, Cold Spring Harbor Laboratory, Cold Spring Harbor, N.Y.
Schell, J, 1987, *Science*, 237:1176-1183.
Smith and Waterman, 1981, *Adv. Appl. Math.*, 2:482.
Tai et al., 1999, *Proc. Natl. Acad. Sci. U.S.A*, 96: 14153-14158.
U.S. Pat. No. 4,407,956.
Van der Biezen et al., 2000, *Plant J.*, 29: 439-51.
Vasil I. R. (ed.), 1986, Cell Culture and Somatic Cell Genetics of Plants, Acad. Press, Orlando, Vol. 1, 1984, and Vol. III.
Wu and Grossman Eds; 1987, Methods in Enzymology Vol. 153 ("Recombinant DNA Part D"), Academic Press.
Xiao et al., 2001, *Science*, 291:118-120.
Zhang and Klessig, 2001, *Trends in Plant Sci.*, 6, 520-527.

That which is claimed is:

1. A method of enhancing disease resistance to pathogen in a plant, the method comprising:
   introducing into the plant a vector or expression cassette expressing an interfering nucleotide sequence comprising at least 17 contiguous nucleotides complementary to SEQ ID NO: 1, wherein SEQ ID NO: 1 is a nucleotide sequence of a defense-associated protein phosphatase type 2C one (DAPP1) gene and wherein the interfering nucleotide sequence inhibits the genetic expression of the DAPP1 gene or a DAPP1 homolog, and
   selecting a plant that exhibits increased disease resistance to a pathogen in the plant compared to an untransformed plant.

2. The method according to claim 1, wherein the plant is selected from the group consisting of *Arabidopsis, Brassica, Raphanus, Sinapis, Atropa, Capsicum, Hyoscyamus, Lycopersicon, Nicotiana, Solanum, Oryza, Petunia, Digitalis, Majorana, Cichorium, Helianthus, Lactuca, Bromus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, Phaseolus, Pisum, Hordeum, Beta* and *Datura*.

3. The method according to claim 1, wherein the disease pathogen is a bacterial or fungal pathogen.

4. The method according to claim 1, wherein the expression cassette further comprises a promoter.

5. The method according to claim 4, wherein the promoter is inducible.

6. The method according to claim 1, wherein the pathogen is *E. cichoracearum; E. orontii; E. lycopersicii; E. cruciferarum; Peronospora parasitica* or *P. syringae*.

* * * * *